US010584383B2

(12) United States Patent
Thum et al.

(10) Patent No.: US 10,584,383 B2
(45) Date of Patent: Mar. 10, 2020

(54) MITOCHONDRIAL NON-CODING RNAS FOR PREDICTING DISEASE PROGRESSION IN HEART FAILURE AND MYOCARDIAL INFARCTION PATIENTS

(71) Applicants: Institut Pasteur de Lille (IPL), Lille (FR); Medizinische Hochschule Hannover, Hannover (DE); Institut National de la Santé et de la Recherche Médicale (INSERM), Paris (FR); Université de Lille 2 (Lille 2)—University of Law and Health, Lille (FR); Centre Hospitalier Universitaire Lille (CHU), Lille (FR)

(72) Inventors: Thomas Thum, Hannover (DE); Regalla Kumarswamy, Hannover (DE); Florence Pinet, Paris (FR); Christophe Bauters, Lille (FR); Pascal De Groote, Lille (FR)

(73) Assignees: MEDIZINISCHE HOCHSCHULE HANNOVER, Hannover (DE); INSTITUT NATIONAL DE LA SANTÉ ET DE LA RECHERCHE MÉDICALE (INSERM), Paris (FR); UNIVERSITÉ DE LILLE 2 (LILLE 2)—UNIVERSITY OF LAW AND HEALTH, Lille (FR); CENTRE HOSPITALIER UNIVERSITAIRE LILLE (CHU), Lille (FR); INSTITUT PASTEUR DE LILLE (IPL), Lille (FR)

( * ) Notice: Subject to any disclaimer, the term of this patent is extended or adjusted under 35 U.S.C. 154(b) by 0 days.

(21) Appl. No.: 15/126,927

(22) PCT Filed: Mar. 18, 2015

(86) PCT No.: PCT/EP2015/055713
§ 371 (c)(1),
(2) Date: Sep. 16, 2016

(87) PCT Pub. No.: WO2015/140224
PCT Pub. Date: Sep. 24, 2015

(65) Prior Publication Data
US 2017/0114409 A1 Apr. 27, 2017

(30) Foreign Application Priority Data
Mar. 18, 2014 (EP) .................................... 14160577

(51) Int. Cl.
C07H 21/02 (2006.01)
C07H 21/04 (2006.01)
C12Q 1/68 (2018.01)
C12Q 1/6883 (2018.01)

(52) U.S. Cl.
CPC ...... *C12Q 1/6883* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 5,474,796 A * 12/1995 Brennan ............. B01J 19/0046
422/547
2012/0122958 A1 5/2012 Dawson et al.

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Wu (Journal of pathology 2001 vol. 195 p. 53). (Year: 2001).*
Newton et al (Journal of Computational Biology 2001 vol. 8 p. 37) (Year: 2001).*
International Search Report and Written Opinion for International Patent Application PCT/EP2015/055713 dated May 18, 2015.
Li, Danhua et al., "Transcriptome Analysis Reveals Distinct Patterns of Long Noncoding RNAs in Heart and Plasma of Mice with Heart Failure," PLOS ONE, (2013) 8(10): e77938.
Yang, Kai-Chien et al., "Deep RNA Sequencing Reveals Dynamic Regulation of Myoacardial Noncoding RNAs in Failing Human Heart and Remodeling with Mechanical Circulatory Support," Circulation, (2014) 129 (9): 1009-1021.
Anonymous, "Arraystar Human Lnc RNA Microarray V2.0 (Agilent_033010 Probe Name Version)," Retrieved from URL:http://www.ncbi.nlm.nih.gov/geo/query/acc.cgi?acc=GPL15314 [retrieved on Jul. 21, 2014].
Ishii, Nobuaki et al., "Identification of a Novel Non-coding RNA, MIAT, that Confers Risk of Myocardial Infarction," Journal of Human Genetics, Springer-Verlag, (2006) 51(12): 1087-1099.
Papait, Roberto et al., "Long Noncoding RNA: A New Player of Heart Failure?," Journal of Cardiovascular Translational Research, (2013) 6(6): 876-883.

(Continued)

*Primary Examiner* — Katherine D Salmon
(74) *Attorney, Agent, or Firm* — Hunton Andrews Kurth LLP

(57) ABSTRACT

The present invention relates to a method for predicting mortality of a test patient with chronic heart failure comprising based on detecting the expression level of one or more long non-coding RNAs (lncRNAs) selected from SEQ ID NOs 1 to 8. The present invention also relates to a method for predicting cardiac remodeling after myocardial infarction in a test patient based on detecting the expression level of one or more lncRNAs selected from SEQ ID NOs 1 to 8.

Figure 1:
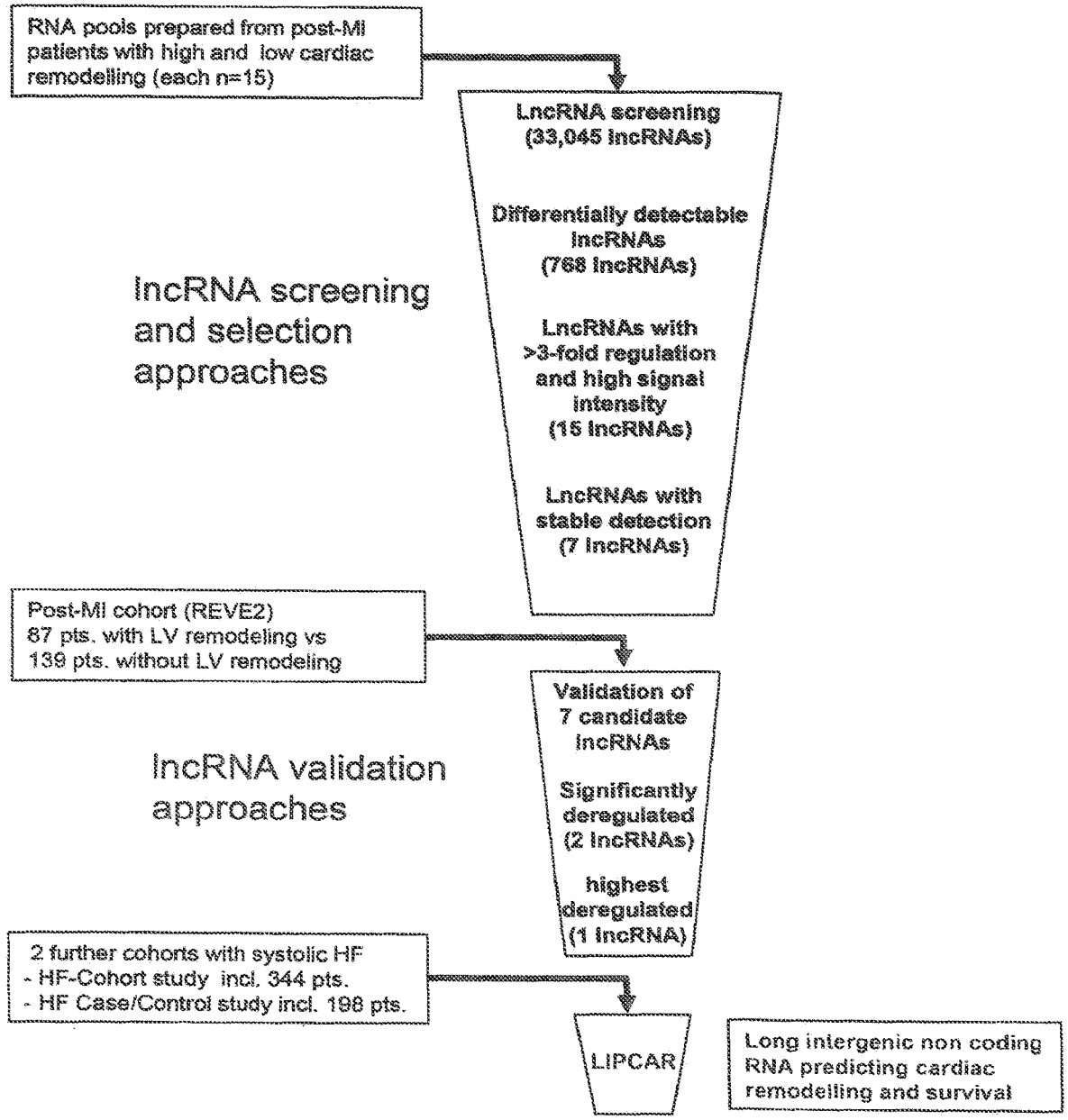

13 Claims, 5 Drawing Sheets
Specification includes a Sequence Listing.

(56) References Cited

OTHER PUBLICATIONS

Peters, Tim et al., "Missing Links in Cardiology: Long non-coding RNAs Enter the Arena," Pflugers Archiv—Eur J. Physiol., (2014) 466(6)1177-1187.

Rackham, Oliver et al., "Long noncoding RNAs are Generated from the Mitochondrial Genome and Regulated by Nuclear-Encoded Proteins," RNA, (2011) 17 (12): 2085-2093.

Kumarswamy, Regalia et al., "Circulating Long Noncoding RNA, LIPCAR, Predicts Survival in Patients with Heart Failure," Circulation Research, (2014) 114 (10): 1569-1575.

Zangrando, Jennifer et al., "Identification of Candidate Long Noncoding RNAs in Response to Myocardial Infarction," BMC Genomics, (2014) 15 (1): 460.

* cited by examiner

MITOCHONDRIAL NON-CODING RNAS FOR PREDICTING DISEASE PROGRESSION IN HEART FAILURE AND MYOCARDIAL INFARCTION PATIENTS

CROSS REFERENCE TO RELATED APPLICATIONS

This application is a U.S. National Phase of International Patent Application PCT/EP2015/055713, filed Mar. 18, 2015, which claims priority to European Patent Application No. 14160577.4, filed Mar. 18, 2014, the contents of each are hereby incorporated by reference in their entireties.

The present invention relates to a method for predicting mortality of a test patient with chronic heart failure comprising (a) detecting the expression level of one or more long non-coding RNAs (lncRNAs) selected from SEQ ID NOs 1 to 8 in a sample obtained from said test patient with chronic heart failure, (b) comparing said expression level of the one or more lncRNAs with the expression level of these one or more lncRNAs in a sample obtained from control patients with chronic heart failure, wherein the control patients were alive at least about three years after diagnosis of the chronic heart failure, and a greater than 2-fold overexpression of at least one of the one or more lncRNAs in the test patient's sample as compared to the control patient's sample is indicative of an enhanced likelihood for future cardiovascular death of the test patient; and/or (b') comparing said expression level of the one or more lncRNAs with the expression level of these one or more lncRNAs in a sample obtained from control patients with chronic heart failure, wherein the control patients died from a cardiovascular event within about three years after diagnosis of chronic heart failure, and a greater than 2-fold underexpression of at least one of the one or more lncRNAs in the test patient's sample as compared to the control patient's sample is indicative of an enhanced likelihood for the long term survival of the test patient. The present invention also relates to a method for predicting cardiac remodeling after myocardial infarction in a test patient comprising (a) detecting the expression level of one or more lncRNAs selected from SEQ ID NOs 1 to 8 in a sample obtained from said test patient after myocardial infarction, and (b) comparing said expression level of the one or more lncRNAs with the expression level of these one or more lncRNAs in a sample obtained from control patients after myocardial infarction, wherein the control patients did not show cardiac remodeling after myocardial infarction, wherein (i) the samples have been obtained from said test patient and from said control patients within a time frame of about two weeks after myocardial infarction, and a greater than 2-fold underexpression of at least one of the one or more lncRNAs in the test patient's sample as compared to the control patient's sample is indicative for future cardiac remodeling in the test patient, and/or (ii) the samples have been obtained from said test patient and from said control patients more than about two weeks after myocardial infarction, and a greater than 2-fold overexpression of at least one of the one or more lncRNAs in the test patient's sample as compared to the control patient's sample is indicative for future cardiac remodeling in the test patient.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The existence of extracellular nucleic acids is known for several decades (Mandel P and Metais P. Les acides nucléiques du plasma sanguin chez l' homme. *C R Acad Sci Paris*. 1948; 142: 241-243). A diagnostic potential of RNA in body fluids was realized after the initial discovery of specific extracellular RNAs in plasma of cancer patients (Kang Y and Massague J. Epithelial-mesenchymal transitions: twist in development and metastasis. *Cell*. 2004; 118: 277-279, and Antos C L et al., Activated glycogen synthase-3 beta suppresses cardiac hypertrophy in vivo. *Proc Natl Acad Sci USA*. 2002; 99: 907-912). Long non-coding RNAs (lncRNAs) are conventionally defined as a transcript longer than 200 nucleotides in length with lack of protein-coding capability (Kung J T et al., noncoding RNAs: past, present, and future. *Genetics*. 2013; 193: 651-669). Recognition of the roles of lncRNAs in human disease has unveiled new mechanistic understanding and will lead to novel diagnostic and therapeutic approaches (Batista P J and Chang H Y. Long noncoding RNAs: cellular address codes in development and disease. *Cell*. 2013; 152: 1298-1307). LncRNAs often form secondary structures, and relatively more stable, which facilitate their detection as free nucleic acids in body fluids such as urine and blood (Reis E M and Verjovski-Almeida S. Perspectives of Long Non-Coding RNAs in Cancer Diagnostics. *Front Genet*. 2012; 3: 32). Due to their well-established association with various cancers, lncRNAs have been previously investigated for their potential role as cancer biomarkers in body fluids. A prostate specific lincRNA PCA3 in urine has been identified as the most specific biomarker for the detection of prostate cancer with higher specificity compared to the widely used PSA (prostate-specific antigen) test (de Kok at al., DD3(PCA3), a very sensitive and specific marker to detect prostate tumors. *Cancer Res*. 2002; 62: 2695-2698; and Hessels D et al., DD3(PCA3)-based molecular urine analysis for the diagnosis of prostate cancer. *Eur Urol*. 2003; 44: 8-15; discussion 15-6). The PCA3 assay has been approved for detection of prostate cancer, and is readily available for clinical use. In addition, several other studies have highlighted the potential of lncRNA as candidate biomarkers for the detection of various cancers (Kim K et al., HOTAIR is a negative prognostic factor and exhibits pro-oncogenic activity in pancreatic cancer. *Oncogene*. 2013; 32: 1616-1625; Kumarswamy R and Thum T. Non-coding RNAs in cardiac remodeling and heart failure. *Circ Res*. 2013; 113: 676-689; and Savoye C et al., REmodelage VEntriculaire study group. Left ventricular remodeling after anterior wall acute myocardial infarction in modern clinical practice (from the REmodelage VEntriculaire [REVE] study group). *Am J Cardiol*. 2006; 98: 1144-1149).

Notwithstanding the potential use potential of lncRNA as biomarkers, for the vast majority of diseases, in particular for cardiovascular diseases, their role as biomarkers is yet unexplored. However, cardiovascular diseases are the leading cause of death (Hoyert D and Xu J. Deaths: Preliminary Data for 2011, *Natl Vital Stat Rep*. 2012; 61: 1-65). Despite advances in understanding and treatment of HF, it still has a poor prognosis (Emdin M et al., Old and new biomarkers of heart failure. *Eur J Heart Fail*. 2009; 11: 331-335). Hence, there is an ongoing need for new biomarkers and diagnostic methods for cardiovascular diseases. This need is addressed by the present invention.

The present invention thus relates in a first aspect to a method for predicting mortality of a test patient with chronic heart failure comprising (a) detecting the expression level of one or more lncRNAs selected from SEQ ID NOs 1 to 8 in a sample obtained from said test patient with chronic heart failure, (b) comparing said expression level of the one or more lncRNAs with the expression level of these one or more lncRNAs in a sample obtained from control patients with chronic heart failure, wherein the control patients were alive at least about three years after diagnosis of the chronic heart failure, and a greater than 2-fold overexpression of at least one of the one or more lncRNAs in the test patient's sample as compared to the control patient's sample is indicative of an enhanced likelihood for future cardiovascular death of the test patient; and/or (b') comparing said expression level of the one or more lncRNAs with the expression level of these one or more lncRNAs in a sample obtained from control patients with chronic heart failure, wherein the control patients died from a cardiovascular event within about three years after diagnosis of chronic heart failure, and a greater than 2-fold underexpression of at least one of the one or more lncRNAs in the test patient's sample as compared to the control patient's sample is indicative of an enhanced likelihood for the long term survival of the test patient.

As can be taken from the wording of this method, the method starts with using isolated samples. Accordingly, the method is in general performed in vitro and preferably does not comprise an invasive step for obtaining the sample from a patient.

The method according to the first aspect of the invention may also encompass detecting and comparing the expression level of one or more lncRNAs being with increased preference at least 90%, at least 92%, at least 94%, at least 96%, at least 98%, at least 99%, and at least 99.5% identical to any one of SEQ ID NOs 1 to 8. Means and methods for determining sequence identity are known in the art. Preferably, the BLAST (Basic Local Alignment Search Tool) program is used for determining the sequence identity with regard to one or more lncRNAs selected from SEQ ID NOs 1 to 8. The method according to the first aspect of the invention may furthermore encompass detecting and comparing the expression level of one or more lncRNAs differing with increasing preference by no more than 10, such as 5, 4, 3, 2 or 1 nucleotide(s) from any one of SEQ ID NOs 1 to 8. The nucleotide differences may be the addition, deletion and/or substitution of nucleotide(s). The sequences the expression of which is compared, while being homologous, may also differ from each other with increasing preference by no more than 10, such as 5, 4, 3, 2 or 1 nucleotide(s).

The term "predicting mortality" as used herein defines determining the future likelihood whether a patient suffering from chronic heart failure will die from cardiovascular death or will survive for a long term. The long term is with increasing preference at least about 2 years, at least about 3 years and at about least 5 years.

In this connection "cardiovascular death" is death caused by a cardiovascular disease, which disease comprises in accordance with the invention a chronic heart failure. The term "cardiovascular event" refers to any incident that may cause damage to the heart muscle. Cardiovascular disease is the leading cause of deaths worldwide. An estimated 17.3 million people died from a cardiovascular event in 2008, representing 30% of all global deaths (Global status report on noncommunicable diseases 2010, Geneva, World Health Organization, 2011). Of these deaths, an estimated 7.3 million were due to coronary heart disease and 6.2 million were due to stroke. The number of people who die from cardiovascular event, mainly from heart disease and stroke, is expected to increase to reach 23.3 million by 2030.

The term "chronic heart failure" means that heart is unable to provide sufficient pump action to maintain blood flow to meet the needs of the body. Heart failure can cause a number of symptoms including shortness of breath, leg swelling and exercise intolerance. The condition is diagnosed by patient physical examination and confirmed with echocardiography. Blood tests can additionally help to determine the cause. Common causes of heart failure include myocardial infarction and other forms of coronary artery disease, hypertension, valvular heart disease, and cardiomyopathy.

The term "sample" designates a tissue sample or preferably a body fluid sample. The body fluid sample is preferably selected from blood, serum, plasma, urine, salvia, amniotic fluid, cerebrospinal fluid and lymph.

The "patient" or "subject" referred to herein is human.

The term "ncRNA" or "non-coding RNA" as used herein designates a functional RNA molecule that is not translated into a protein. The DNA sequence from which a non-coding RNA is transcribed is often called in the art an RNA gene. The term "lncRNA" or "long non-coding RNA" as commonly used in the art designates an ncRNA comprising more than 200 nucleotides. SEQ ID NOs 1 to 8 cover a length range of 346 to 2509 nucleotides.

The term "detecting the expression level of ncRNA" means determining the amount or yield of the ncRNA. The lncRNAs are initially expressed within a cell. It was found in accordance with the present invention that the lncRNAs of SEQ ID NOs 1 to 8 can be detected in the sample of a patient, in particular a blood sample, such as serum or plasma sample. This shows that the lncRNAs leave the cells and are stable outside the cells (See FIG. 7). An lncRNA being "expressed in a sample" is therefore a lncRNA whose expression level can be detected in the sample by means and methods being further detailed herein below. Hence, the expression level of one or more lncRNAs selected from SEQ ID NOs 1 to 8 can be detected in a sample as required by the methods of the invention. An ncRNA is overexpressed in a test sample if the amount or yield of the ncRNA is greater as compared to the amount or yield of the corresponding ncRNA in a control sample. Likewise, an ncRNA is underexpressed in a test sample if the amount or yield of the ncRNA is less as compared to the amount or yield of the corresponding ncRNA in a control sample. In this context the term "corresponding ncRNA" means, for example, that the expression level of the lncRNA of SEQ ID NO: 1 in the test sample is compared to the expression level of the lncRNA of SEQ ID NO: 1 in the control sample, or likewise that the expression level of the lncRNA of SEQ ID NO: 2 in the test sample is compared to the expression level of the lncRNA of SEQ ID NO: 2 in the control sample. This applies mutatis mutandis for scenarios where the expression of more than one lncRNA selected from SEQ ID NOs 1 to 8 is determined. For instance, if the expression level of all eight lncRNAs of SEQ ID NOs 1 to 8 is determined in the test sample it is compared to the expression level of all eight lncRNAs of SEQ ID NOs 1 to 8 in the control sample.

The expression level in the samples can be quantified by any suitable means and methods available from the art. In general relative and absolute quantification means and methods can be used. In absolute quantification no known standards or controls are needed. The expression level can be directly quantified. As well-known in the art, absolute quantification may rely on a predetermined standard curve. In relative quantification the expression level is quantified relative to a reference (such as known control expressions levels). Also in the absence of controls, one can relatively quantify the expression level when comparing e.g. fluorescence intensities. Suitable means and methods are further detailed herein below.

Any suitable method may be used in accordance with the invention to determine the the expression level of one or more of the lncRNA of SEQ ID NOS. 1 to 8. Methods to assess RNA concentration may, for example, comprise measuring the fluorescence intensity of dyes that bind to nucleic acids and selectively fluoresce when bound. Such methods comprise a reverse transcription reaction and the production of cDNA, wherein the amount of the cDNA is determined thereby indirectly determining the amount of the RNA. The fluorescent-based method is particularly useful for cases where the RNA concentration is too low to accurately assess some with spectrophotometry and/or in cases where contaminants absorbing at 260 nm make accurate quantification by spectrophotometry difficult or impossible. Methods comprising measuring the fluorescence intensity will be further detailed herein below.

When comparing the expression level of the one or more lncRNAs between different samples reliability of the comparison is preferably improved by including an invariant endogenous control (expression of a reference gene) to correct for potential sample to sample variations. Such normalization with respect to an invariant endogenous control is routinely performed in the art. For example, means and methods for expression level normalization, e.g. in real-time RT-PCR (see, for example, Bustin, Journal of Molecular Endocrinology, (2002) 29, 23-39) or micro-array expression analysis (see, for example, Calza and Balwitan, Methods Mol Biol. 2010; 673:37-52) are well-established. Also methods for normalization of the expression levels of small RNA sequences are established (see, for example, Mestdagh et al. (2009) Genome Biol.; 10(6):R64). In case RT-PCR or a micro-array is used to determine the expression levels in accordance with the present invention, the expression levels are preferably normalized to a spiked-in RNA (see, for example, McCormick et al. (2011), Silence, 2:2). Known amounts of a spiked-in RNA are mixed with the sample during preparation. More preferably the RNA is externally spiked-in to plasma and/or serum before the RNA isolation process is carried out, in which case the samples are plasma and/or serum. The spiked-in RNA technology is well-known and commercial kits are available from a number of manufacturers. The spiked-in RNA is preferably a spiked-in C. elegans RNA.

The test sample and the control sample are preferably obtained from the patients with chronic heart failure directly after the patients have been diagnosed as having chronic heart failure. In this connection "directly" means with increasing preference within a time frame of about 3 months, about 1 month, about two weeks and about one week.

Although numerous studies have investigated small RNAs such as microRNAs (miRNAs) as potential biomarkers for heart failure (HF) (Kumarswamy R and Thum T. Non-coding RNAs in cardiac remodeling and heart failure. Circ Res. 2013; 113: 676-689), the diagnostic utility of circulating lncRNAs in heart diseases has to the best knowledge of the inventors never been investigated. The examples herein below evidence the potential of using the expression levels of the lncRNAs of SEQ ID NOs 1 to 8 in a sample, in particular in a plasma sample, as prognostic biomarkers for heart failure. The initial lncRNA screening which led to the identification of the lncRNAs of SEQ ID NOs 1 to 8 was performed according to the level of left ventricular (LV) remodeling in a prospective echocardiographic study of patients after myocardial infarction (MI). LV remodeling, which remains frequent in modern clinical practice (Savoye C et al., Left ventricular remodeling after anterior wall acute myocardial infarction in modern clinical practice (from the REmodelage VEntriculaire [REVE] study group). Am J Cardiol. 2006; 98: 1144-1149) is a well-known surrogate of HF after MI (St John Sutton M et al., Quantitative two-dimensional echocardiographic measurements are major predictors of adverse cardiovascular events after acute myocardial infarction. The protective effects of captopril. Circulation. 1994; 89: 68-75). The lncRNA of SEQ ID NO: 1 was tested for its association with HF, and for its prognostic value in two further independent populations of systolic heart failure patients.

It has been found in accordance with the invention that all of the lncRNAs of SEQ ID NOs 1 to 8 are encoded by the mitochondrial genome. The expression of the mitochondrial genome is well-studied. It is known that transcription of both, the heavy (H) and light (L), strands of mtDNA gives rise to large polycistronic transcripts covering almost the entire genome (Shabel (2008), Am J Pathol, 172(6):1445-1456). These long precursor mitochondrial transcripts undergo processing to form functional RNAs as well as ncRNAs. Furthermore, the expression of the mitochondrial genome is regulated by a small set of cellular components, including mainly a monomeric RNA polymerase (POL-RMT), and mitochondrial transcription factors A (TFAM) and B2 (TFB2M) (Falkenberg, et al. (2007), Annu Rev Biochem 76:679-99). It is thus evident that the expression levels of the lncRNAs of SEQ ID NOs 1 to 8 are linked to each other and are controlled by a common cellular machinery.

As explained above, all of the lncRNAs of SEQ ID NOs 1 to 8 were studied in patients shortly after myocardial infarction (MI). It was found that all of SEQ ID NOs 1 to 8 are underexpressed shortly after MI in patients which later developed left ventricular (LV) remodeling. Furthermore, the lncRNAs of SEQ ID NO: 1 was tested for its association with HF. It was unexpectedly found that SEQ ID NO: 1 is overexpressed (as opposed to an underexpression directly after MI) in chronic heart failure patients who died within three years after the initial diagnosis of the chronic heart failure. Although this was only experimentally confirmed for SEQ ID NO: 1 it is clear in view of (i) the linked and commonly controlled expression level of mitochondrial transcripts as well as (ii) the fact that after MI all of SEQ ID Nos 1 to 8 behave in the same way—namely underexpression—that the lncRNAs of SEQ ID NOs 2 to 8 just behave as SEQ ID NO: 1. Hence, also the lncRNAs of SEQ ID NOs 2 to 8 are in accordance with the invention expected to be overexpressed in chronic heart failure patients who die within three years after the initial diagnosis of the chronic heart failure.

In accordance with a preferred embodiment of the first aspect of the invention, the chronic heart failure is systolic heart failure.

Diastolic heart failure (DHF) and systolic heart failure (SHF) are the two common clinical subsets of chronic heart failure (Chatterjee et al. (2007), Journal of Cardiac Failure 13(7): 569-576). Systolic dysfunction results from impaired contractile or pump function of the heart while diastolic dysfunction results from impaired ventricular relaxation. Compliance is not always associated with clinical heart failure characterized by signs and symptoms of low cardiac output or of congestion. Furthermore, in SHF, diastolic dysfunction as assessed by changes in the ventricular filling features is common, particularly in advanced heart failure. In diastolic heart failure, left ventricular systolic performance, function and contractility in general remain normal. For diagnosing whether a chronic heart failure is DHF or SHF thus the left ventricular ejection fraction is measured. If ejection fraction is preserved it is DHF, and if it is reduced it is SHF.

In systolic heart failure approximately 50% of deaths are sudden and the rate of sudden death in systolic heart failure is 6 to 9 times higher compared with that in the general population (American Heart Association. Heart disease and stroke statistics 2003 update. Dallas, Tex.: American Heart Association; 2002). It is therefore of particular relevance to provide methods for predicting mortality of a patient with systolic heart failure.

The present invention relates in a second aspect to a method for predicting cardiac remodeling after myocardial infarction in a test patient comprising (a) detecting the expression level of one or more lncRNAs selected from SEQ ID NOs 1 to 8 in a sample obtained from said test patient after myocardial infarction, and (b) comparing said expression level of the one or more lncRNAs with the expression level of these one or more lncRNAs in a sample obtained from control patients after myocardial infarction, wherein the control patients did not show cardiac remodeling after myocardial infarction, wherein (i) the samples have been obtained from said test patient and from said control patients within a time frame of about about two weeks after myocardial infarction, and a greater than 2-fold underexpression of at least one of the one or more lncRNAs in the test patient's sample as compared to the control patient's sample is indicative for future cardiac remodeling in the test patient, and/or (ii) the samples have been obtained from said test patient and from said control patients more than about two weeks after myocardial infarction, and a greater than 2-fold overexpression of at least one of the one or more lncRNAs in the test patient's sample as compared to the control patient's sample is indicative for future cardiac remodeling in the test patient.

As can also be taken from the wording of this method, the method starts with using isolated samples. Accordingly, the method is in general performed in vitro and preferably does not comprise an invasive step for obtaining the sample from a patient.

The method of the second aspect invention may also encompass detecting and comparing the expression level of one or more lncRNAs being with increased preference at least 90%, at least 92%, at least 94%, at least 96%, at least 98%, at least 99%, and at least 99.5% identical to any one of SEQ ID NOs 1 to 8. The method according to the second aspect of the invention may furthermore encompass detecting and comparing the expression level of one or more lncRNAs differing with increasing preference by no more than 10, such as 5, 4, 3, 2 or 1 nucleotide(s) from any one of SEQ ID NOs 1 to 8. The sequences the expression of which is compared, while being homologous, may also differ from each other with increasing preference by no more than 10, such as 5, 4, 3, 2 or 1 nucleotide(s).

The term "myocardial infarction" or "MI" defines an event commonly known as a heart attack. It occurs when blood stops flowing properly to part of the heart and the heart muscle is injured due to insufficient oxygen supply. Usually this occurs because one of the coronary arteries that supplies blood to the heart develops a blockage, for example, due to an unstable buildup of white blood cells, cholesterol and fat.

The term "cardiac remodeling" as used herein refers to the changes in size, shape, structure and physiology of the heart after MI. After MI, a series of histopathological and structural changes may occur, which in most cases involve the left ventricular myocardium and lead to progressive decline in left ventricular performance. Ultimately, cardiac remodeling may result in diminished contractile (systolic) function and reduced stroke volume.

All of the lncRNAs of SEQ ID NOs 1 to 8 were studied in patients shortly after myocardial infarction (MI). In more detail, the samples were obtained from the patients at discharge, which is in general no longer than within about two weeks calculated from the myocardial infarction event. It was found that all of SEQ ID NOs 1 to 8 are underexpressed shortly after MI in patients which later developed left ventricular (LV) remodeling. In an extension study samples were also obtained from the patients at a later stage after MI, namely at 1 month, 3 months and 12 months after MI. As can be taken from the examples herein below, it was surprisingly found that the lncRNA of SEQ ID NO: 1 is overexpressed in these late stages after MI in patients which later developed left ventricular (LV) remodeling. Although this was only experimentally confirmed for SEQ ID NO: 1 it is again clear in view of (i) the linked and commonly controlled expression level of mitochondrial transcripts as well as (ii) the fact that early after MI all of SEQ ID NOs 1 to 8 behave in the same way that the lncRNAs of SEQ ID NOs 2 to 8 just behave as SEQ ID NO: 1. Hence, also the lncRNAs of SEQ ID NOs 2 to 8 in accordance with the invention expected to be overexpressed in late stages after MI in patients which later developed left ventricular (LV) remodeling. LV remodeling was selected for preparing the examples of the invention as a means to determine cardiac remodeling because most cardiac remodeling is characterized by LV remodeling. However, the method according to the second aspect is not limited to predicting LV remodeling but can be used to predict cardiac remodeling in general.

In accordance with the second aspect of the invention, the sample being obtained from control patients after myocardial infarction is with increasing preference obtained within about 3 months, within about 2 months, within about 1 month, within about two weeks, within about 10 days and within about 1 week after myocardial infarction.

In accordance with a preferred embodiment of the second aspect of the invention, the cardiac remodeling comprises or is left ventricular remodeling.

As discussed, measuring LV remodeling was used in the examples herein below to determine whether a patient suffers from cardiac remodeling. In accordance with the invention, LV remodeling is defined as a more than 20% change in left ventricular end-diastolic volume (LVEDV) between baseline (i.e. directly after MI) and 12 months after MI.

In accordance with a further preferred embodiment of the second aspect of the invention, the time frame of about two weeks is a time frame of about 10 days, preferably a time frame of about 7 days. In accordance with another preferred embodiment of the second aspect of the invention, the more than about two weeks are more than about three weeks, preferably more than about four weeks.

In this connection the term "about" is preferably ±1 day. The term "time frame of about two weeks" means "about 14 days or less", the time frame of about 10 days means "about 10 days or less", and the time frame of about 7 days means "about 7 days or less". More than about two weeks means "longer than about 14 days", more than about three weeks means "longer than about 21 days", more than about four weeks means "longer than about 28 days. The tested samples were obtained from MI patients on the one hand directly after MI (i.e. at discharge) and again at 1 month and later after MI. While the underexpression of the lncRNAs early after MI indicates future cardiac remodeling, the scenario is different at a later stage after MI. At a later stage after MI overexpression of the lncRNAs indicates future cardiac remodeling. It is believed that the reversal point in time of the expression level is around two weeks after the MI event. The time frame is expected to vary between patients. Therefore, in further preferred embodiments the time frame of two weeks is a time frame of 10 days, preferably a time frame of 7 days and/or the more than two weeks are more than three weeks, preferably more than four weeks.

In accordance with a preferred embodiment of the first and second aspect of the invention, the greater than 2-fold under- and/or overexpression is greater than 2.5-fold under- and/or overexpression, preferably greater than 3-fold under- and/or overexpression.

In accordance with the invention, a 2-fold under- and/or overexpression of at least one of the lncRNAs of SEQ ID NOs 1 to 8 is of sufficient value for predicting cardiac remodeling after myocardial infarction and/or predicting mortality of a patient with chronic heart failure. However, it is also known that the confidence level of a diagnostic method may be increased by increasing the expression level threshold which is assumed to be indicative for a certain event. For this reason, the greater than 2-fold under- and/or overexpression is preferably greater than 2.5-fold under- and/or overexpression, more preferably greater than 3-fold under- and/or overexpression.

In accordance with a further preferred embodiment of the first and second aspect of the invention, the test patient and the control patients are matched by one or more of age, sex, diabetes mellitus, heart failure etiology, and race.

Figure 3:
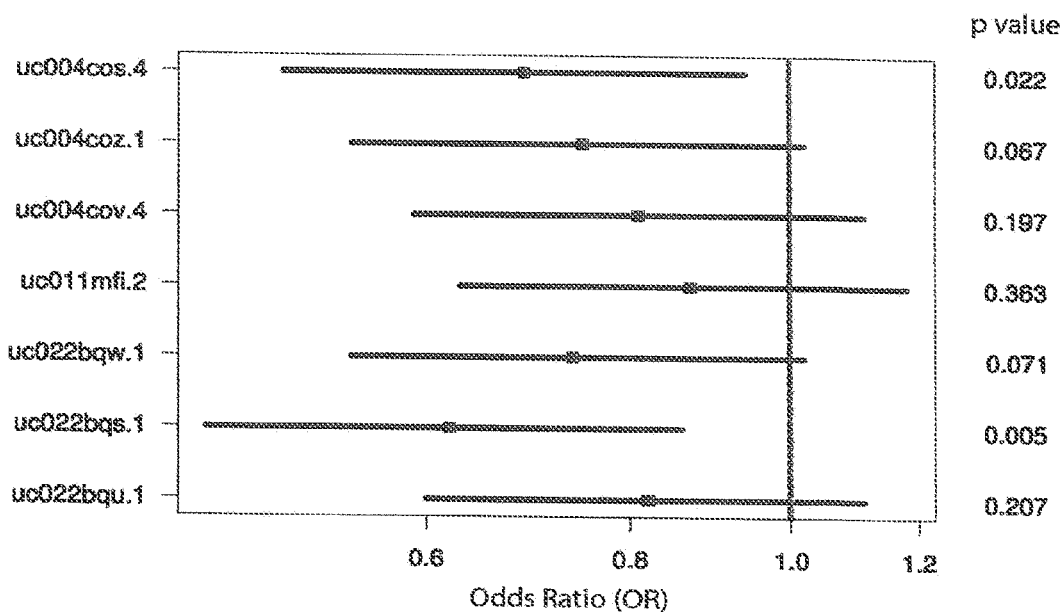

As can be taken from Figure legend 3 the results shown in FIG. 3 were adjusted on age (59 years in both analyzed cohorts) and sex (8% women in both analyzed cohorts). Matching the test patient and the control patients by one or more of age, sex, diabetes mellitus, heart failure etiology, and race will additionally increase the liability of the methods of the invention, since any potential expression level differences caused by differences in age, sex, diabetes mellitus state, heart failure etiology, and/or race can be excluded.

In accordance with a still further preferred embodiment of the first and second aspect of the invention, the control patients are at least 3 patients, preferably a least 5 patients, and more preferably a least 10 patients.

Increasing the number of patients to at least 3 patients, preferably a least 5 patients, and more preferably a least 10 control patients is expected to additionally increase the liability of the methods of the invention, because potential expression level abnormalities in a given control patient are normalized by the other control patients.

In accordance with another preferred embodiment of the first and second aspect of the invention, the detection of the expression level of the one or more lncRNAs comprises (i) quantitative PCR, preferably quantitative real time PCR, or (ii) a template/RNA amplification method followed by determining the expression level of the one or more lncRNAs using a fluorescence- or luminescence-based quantification method.

In quantitative PCR (qPCR), the amount of amplified product is linked to fluorescence intensity using a fluorescent reporter molecule. The point at which the fluorescent signal is measured in order to calculate the initial template quantity can either be at the end of the reaction (endpoint semi-quantitative PCR) or while the amplification is still progressing (real-time qPCR).

In endpoint semi-quantitative PCR, fluorescence data are collected after the amplification reaction has been completed, usually after 30-40 cycles, and this final fluorescence is used to back-calculate the amount of template present prior to PCR.

The more sensitive and reproducible method of real-time qPCR measures the fluorescence at each cycle as the amplification progresses. This allows quantification of the template to be based on the fluorescence signal during the exponential phase of amplification, before limiting reagents, accumulation of inhibitors, or inactivation of the polymerase have started to have an effect on the efficiency of amplification. Fluorescence readings at these earlier cycles of the reaction will measure the amplified template quantity where the reaction is much more reproducible from sample to sample than at the endpoint.

A non-limiting example of a template/RNA amplification method followed by determining the expression level of the one or more lncRNAs using a fluorescence- or luminescence-based quantification method is a method combining transcription mediated amplification (TMA) and a hybridization protection assay (HPA). In more detail, such method may comprise hybridizing one or more oligonucleotides ("capture oligonucleotides") that are complementary to SEQ ID NOs 1 to 8. In case two or more of SEQ ID NOs 1 to 8 are targeted, a separate capture oligonucleotides is used for each sequence selected from SEQ ID NOs 1 to 8. The hybridized target sequences are then captured onto magnetic microparticles that are separated from the sample in a magnetic field. Wash steps may be utilized to remove extraneous components. Target amplification typically occurs via TMA, which is a transcription-based nucleic acid amplification method that utilizes two enzymes, Moloney murine leukemia virus (MMLV) reverse transcriptase and T7 RNA polymerase. A unique set of primers is used for each target sequence selected from SEQ ID NOs 1 to 8. The reverse transcriptase is used to generate a DNA copy (containing a promoter sequence for T7 RNA polymerase) of the target sequence. T7 RNA polymerase produces multiple copies of RNA amplicon from the DNA copy. Detection of lncRNA expression level is achieved by HPA using single-stranded, chemiluminescent-labeled nucleic acid probes that are complementary to the one or more amplicon. Preferably, distinguishably labelled probes are used for each target amplicon. The labeled nucleic acid probes hybridize specifically to the amplicon. A "selection reagent" then differentiates between hybridized and unhybridized probes by inactivating the label on unhybridized probes. During the detection step, the chemiluminescent signal produced by the hybridized probe is measured in a luminometer and is reported as "Relative Light Units" (RLU), thereby quantifying the lncRNA expression level.

In accordance with a more preferred embodiment of the first and second aspect of the invention, the one or more lncRNAs comprise SEQ ID NO: 1 and in the PCR the primers sequences of SEQ ID NOs 19 and 20 are employed for the detection of the expression level of SEQ ID NO: 1.

As can be taken from the examples herein below the primer pair SEQ ID NOs 19 and 20 was advantageously used by the inventors in the context of measuring the expression level of the lncRNAs of SEQ ID NO: 1.

The present invention relates in a third aspect to a method for determining whether a patient has or is at risk of developing a heart failure, comprising detecting the expression of one or more lncRNAs selected from SEQ ID NOs 1 to 8 in a sample obtained from said patient, wherein the patient has or is at risk of developing a heart failure if the expression of one or more lncRNAs selected from SEQ ID NOs 1 to 8 is detected in the sample.

The method according to the third aspect of the invention may also encompass detecting the expression level of one or more lncRNAs being with increased preference at least 90%, at least 92%, at least 94%, at least 96%, at least 98%, at least 99%, and at least 99.5% identical to any one of SEQ ID NOs 1 to 8. The method according to the third aspect of the invention may furthermore encompass detecting the expression level of one or more lncRNAs differing with increasing preference by no more than 10, such as 5, 4, 3, 2 or 1 nucleotide(s) from any one of SEQ ID NOs 1 to 8.

In accordance with the present invention it was surprisingly found that the expression of SEQ ID NOs 1 to 8 could not be detected in healthy subjects but only in patients after MI or in patients having a heart failure. It follows that the expression of SEQ ID NOs 1 to 8 in samples obtained from healthy subjects is absent or below the detection limit. The detection limit is preferably a Ct (cycle threshold) value in a real-time PCR of more than 34, preferably more than 36, more preferably more than 38, and most preferably more than 40. In a real time PCR assay a positive reaction is detected by accumulation of a fluorescent signal. The Ct is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample).

Hence, detecting the expression of one or more of SEQ ID NOs 1 to 8 in sample of a patient indicates that the patient has or is at risk of developing a heart failure. Whether the patient has or is at risk of developing a heart failure can be further assessed by routine diagnosis of the heart. Non-limiting examples of routine diagnostics are echocardiography or an electrocardiogram.

According to a preferred embodiment of the first, second and third aspect of the invention, the one or more lncRNAs is or comprises the lncRNA of SEQ ID NO: 1.

As demonstrated in the examples the lncRNA of SEQ ID NO: 1 (designated uc022bqs.1 in the examples) had the greatest association with LV-remodeling early after MI among the mitochondrial lncRNA of SEQ ID NOs 1 to 8. Thus, SEQ ID NO: 1 has been selected for studying association with LV-remodeling later after MI and with association HF. For these reasons the use of lncRNA of SEQ ID NO: 1 is most preferred among the use of lncRNA of SEQ ID NOs 1 to 8.

It is also preferred within the context of the first, second and third aspect of the invention that the one or more lncRNAs is or comprises the lncRNA of SEQ ID NO: 1 and/or SEQ ID NO: 2. As can be taken from the examples, the lncRNAs of SEQ ID NO: 1 and SEQ ID NO: 2 were both independently shown to be predictive for future cardiac remodeling in patients.

In accordance with a further preferred embodiment of the first, second and third aspect of the invention, the samples are blood and preferably plasma samples.

The term "blood sample" encompasses whole blood as well as any blood-derived sample, in particular plasma or serum. Most preferred the blood sample is a plasma sample.

In accordance with a different preferred embodiment of the first, second and third aspect of the invention, the method comprises prior to the detection of the expression level of the long non-coding RNA a pre-amplification step of the RNA within the test patient's sample and/or the control patient's sample.

Performing a pre-amplification step is of particular advantage in case only low amount of (test and/or control) sample is available. The pre-amplification step allows increasing the amount of RNA within the sample before proceeding to the analysis of the expression level. Means and methods for the pre-amplification of RNA are well known in the art (see, e.g., Vermeulen et al (2009) BMC Res Notes., 2:235). In case both the RNA in the test and control sample is pre-amplified preferably the same method for the pre-amplification step is used such that the RNA relative amount of the test sample as compared to the control sample is maintained. In case only the RNA of the test or control sample is pre-amplified or the two RNA samples are pre-amplified by different methods, the expression level data may have to be normalized for pre-amplification step; see, e.g. Mestdagh et al. (2009), *Genome Biology* 2009, 10:R64.

In accordance with a still further preferred embodiment of the first, second and aspect of the invention, the one or more lncRNAs are at least 3 lncRNAs, preferably at least 5 lncRNAs, and most preferably all 8 lncRNAs.

Employing at least 3 lncRNAs, preferably at least 5 lncRNAs, and preferably most all 8 lncRNAs of SEQ ID NOs 1 to 8 will additionally increase the liability of the methods of the invention. Although the lncRNAs of SEQ ID NOs 1 to 8 are all encoded by the mitochondrial genome, the expression of which is regulated by a common mechanism, employing at least 3 lncRNAs, preferably at least 5 lncRNAs, and preferably most all 8 lncRNAs of SEQ ID NOs 1 to 8 may balance potential differences associated with a particular probe or method used for detecting the expression level of any one of SEQ ID NOs 1 to 8.

The present invention relates in a fourth aspect to a kit for predicting cardiac remodeling after myocardial infarction in a patient and/or predicting mortality of a patient with chronic heart failure and/or predicting heart failure in a patient, said kit comprising means for the detection of the expression level of one or more lncRNAs selected from SEQ ID NOs 1 to 8 and instructions how to use the kit.

The means for the detection of the expression level of one or more lncRNAs selected from SEQ ID NOs 1 to 8 are preferably the means required for (i) a quantitative PCR, preferably quantitative real time PCR, or (ii) a template/RNA amplification method followed by determining the expression level of the one or more lncRNAs using a fluorescence- or luminescence-based quantification method. These means have been further detailed herein above, and may be comprised in the kit. Hence, the means preferably comprise oligonucleotides, such as fluorescent hybridization probes or primers, which specifically hybridize to one or more lncRNAs selected from SEQ ID NOs 1 to 8. Additional ingredients of the kits may be florescent or luminescent dyes, preferably coupled to said oligonucleotides. Also, additional ingredients of the kits may be enzymes, such as a reverse transcriptase and/or a polymerase.

In accordance with the kit of the invention the means for the detection of the expression level of one or more lncRNAs selected from SEQ ID NOs 1 to 8 preferably comprise means for the detection of the lncRNA of SEQ ID NO: 1 and/or SEQ ID NO: 2.

The various components of the kit may be packaged in one or more containers such as one or more vials. The vials may, in addition to the components, comprise preservatives or buffers for storage. In addition, the kit may contain instructions for use.

In accordance with a preferred embodiment of the fourth aspect of the invention, the means are primer pairs used for the specific detection of the expression level of one or more lncRNAs selected from SEQ ID NOs 1 to 8.

In the examples primers pairs were used for the specific detection of the expression level of the lncRNAs of SEQ ID NO 1 to 8 (see Table 6). The primer pairs preferably comprise a primer pair which can be used for the specific detection of the expression level of the lncRNAs of SEQ ID NO: 1. The primer pair which can be used for the specific detection of the expression level of the lncRNAs selected of SEQ ID NO 1 is preferably reflected by SEQ ID NOs 19 and 20.

The figures show:

FIG. 1: Schematic representation of work flow of lncRNA-screening and validation in various populations with heart failure. A total of 1526 samples collected from 246 patients of the REVS 2 cohort (Fertin M et al., Usefulness of serial assessment of B-type natriuretic peptide, troponin I, and C-reactive protein to predict left ventricular remodeling after acute myocardial infarction (from the REVE-2 study). *Am J Cardiol.* 2010; 106: 1410-1416); patients with a first anterior wall Q-wave MI screened for LV-remodeling during the 1-year post-MI period and collected over four different time points (baseline, after one, three and 12 months), 344 patients with chronic heart failure, and 198 patients from a case/control study of patients with chronic heart failure were employed in the present study. This approach identified LIPCAR, a long intergenic non coding RNA predicting cardiac remodeling and survival of heart failure patients. Red dots indicate significantly regulated lncRNAs (>2-fold; p≤0.05). Black dots indicate seven regulated mitochondrial lncRNAs. Black arrow indicates LIPCAR.

Figure 2:
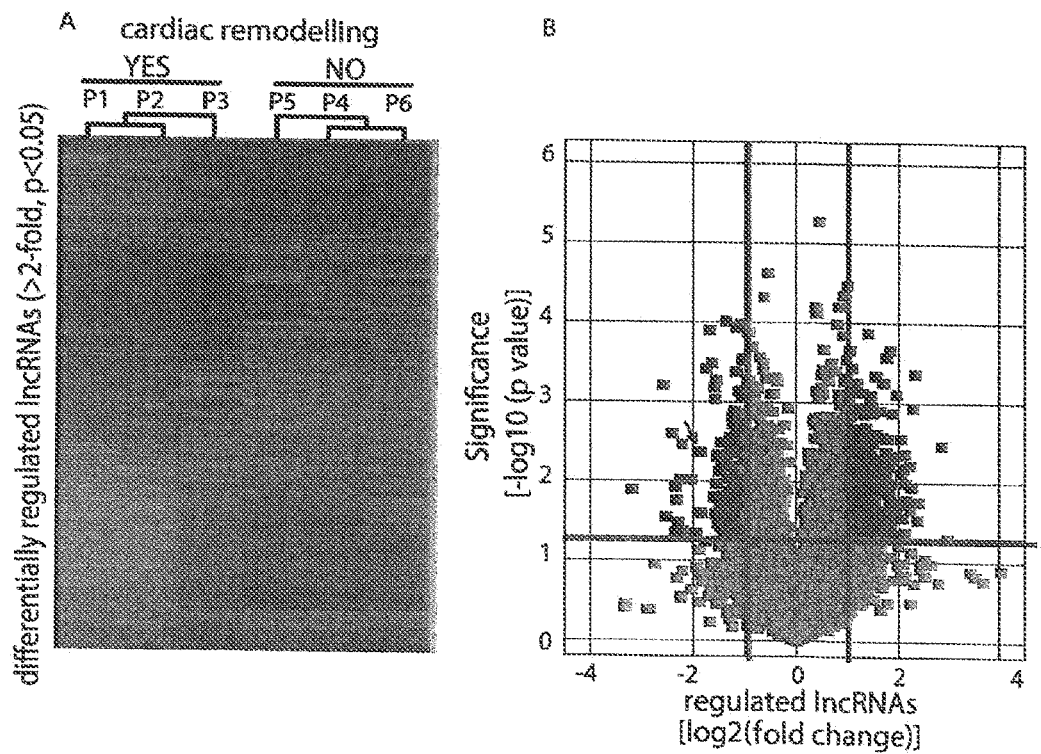

FIG. 2: Hierarchical clustering based on levels of circulating lncRNAs in HF patients with (P1, P2, P3) or without (P4, P5 P6) left ventricular remodeling (A). Volcano plot of fold-change and corresponding p values for each lncRNA after comparison of the two patient groups (remodelers vs non-remodelers) (B).

FIG. 3: The relationship between circulating lncRNAs at baseline and LV-remodeling. Data are given as Odds Ratios (OR) and 95% confidence interval per 1 standard deviation. LV-remodeling is defined as a >20% change in left ventricular end-diastolic volume (LVEDV) from baseline to 1 year follow-up. Analyses were adjusted on age, sex, and baseline LVEDV.

Figure 4:
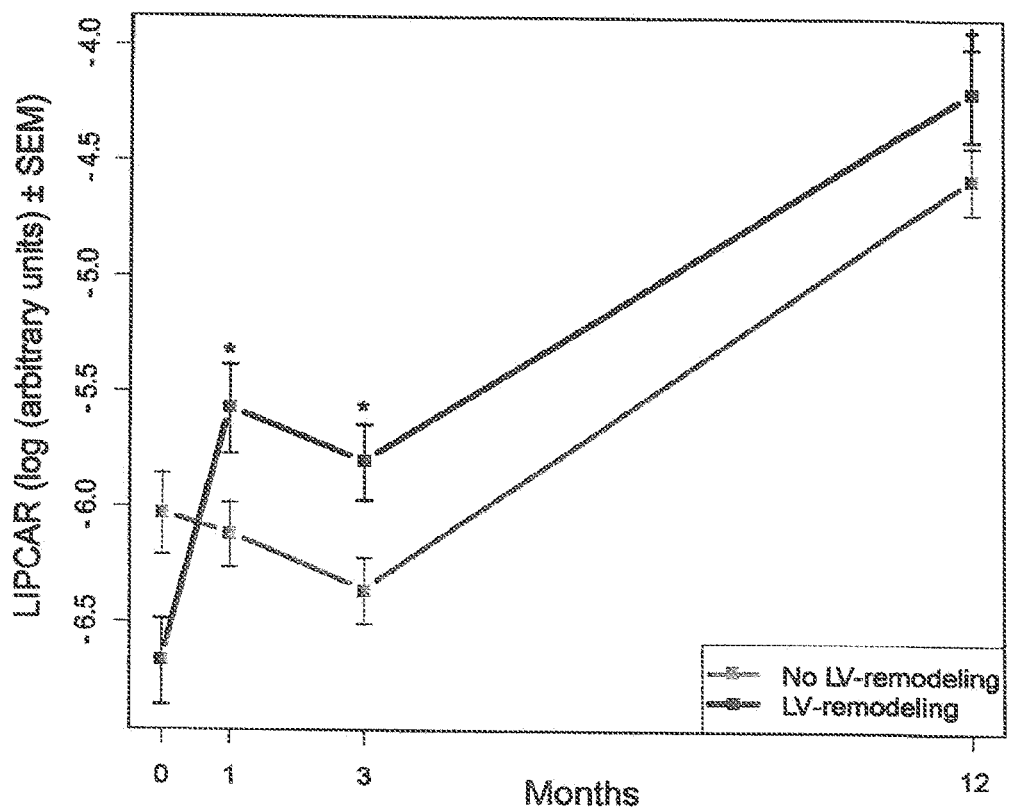

FIG. 4: Levels of LIPCAR at baseline, one month, three months, and 12 months after MI according to the presence/absence of LV-remodeling. LV-remodeling was defined as a >20% change in LVEDV from baseline to 1 year follow-up. * P<0.01 vs no LV-remodeling, † P<0.05 vs no LV-remodeling.

Figure 5:
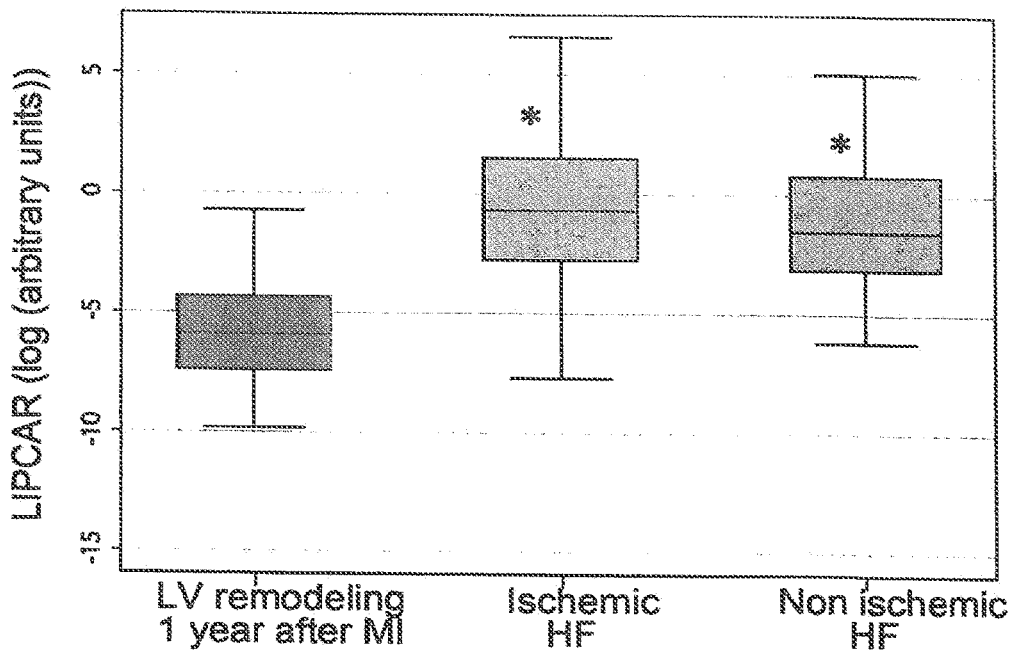

FIG. 5: Levels of LIPCAR in patients with ischemic and non ischemic etiology in the chronic HF cohort. The level of LIPCAR one year after MI in patients with significant LV-remodeling is shown as a reference. *** P<0.0001 vs LV-remodeling 1 year after MI.

Figure 6:
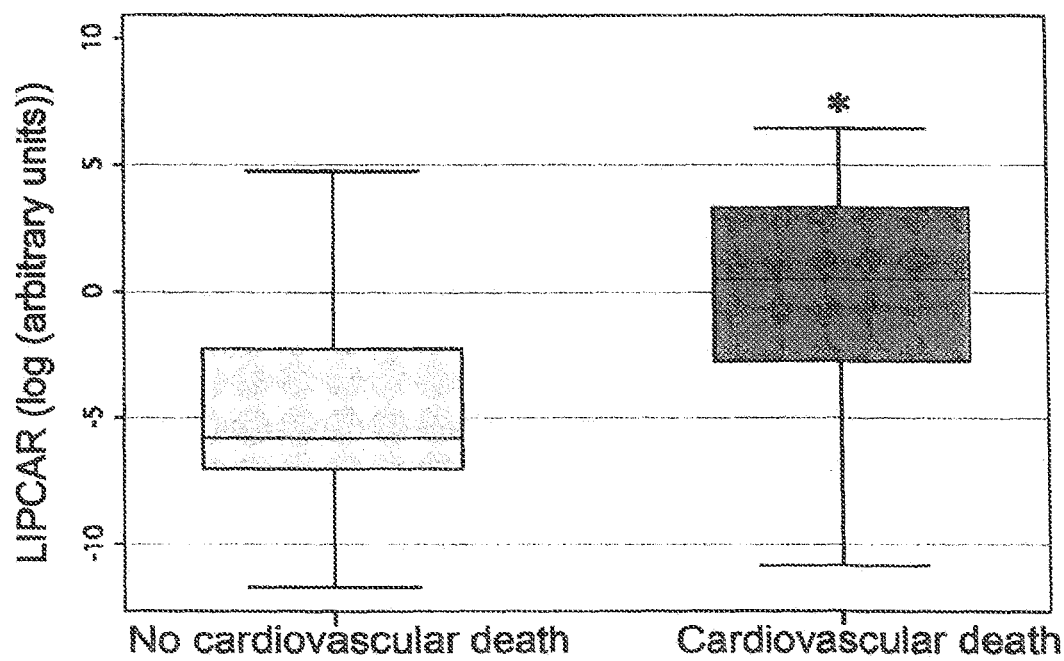

FIG. 6: Levels of LIPCAR in patients with future cardiovascular death vs patients without cardiovascular death in the case/control study. *** P<0.0001 vs No cardiovascular death.

Figure 7:
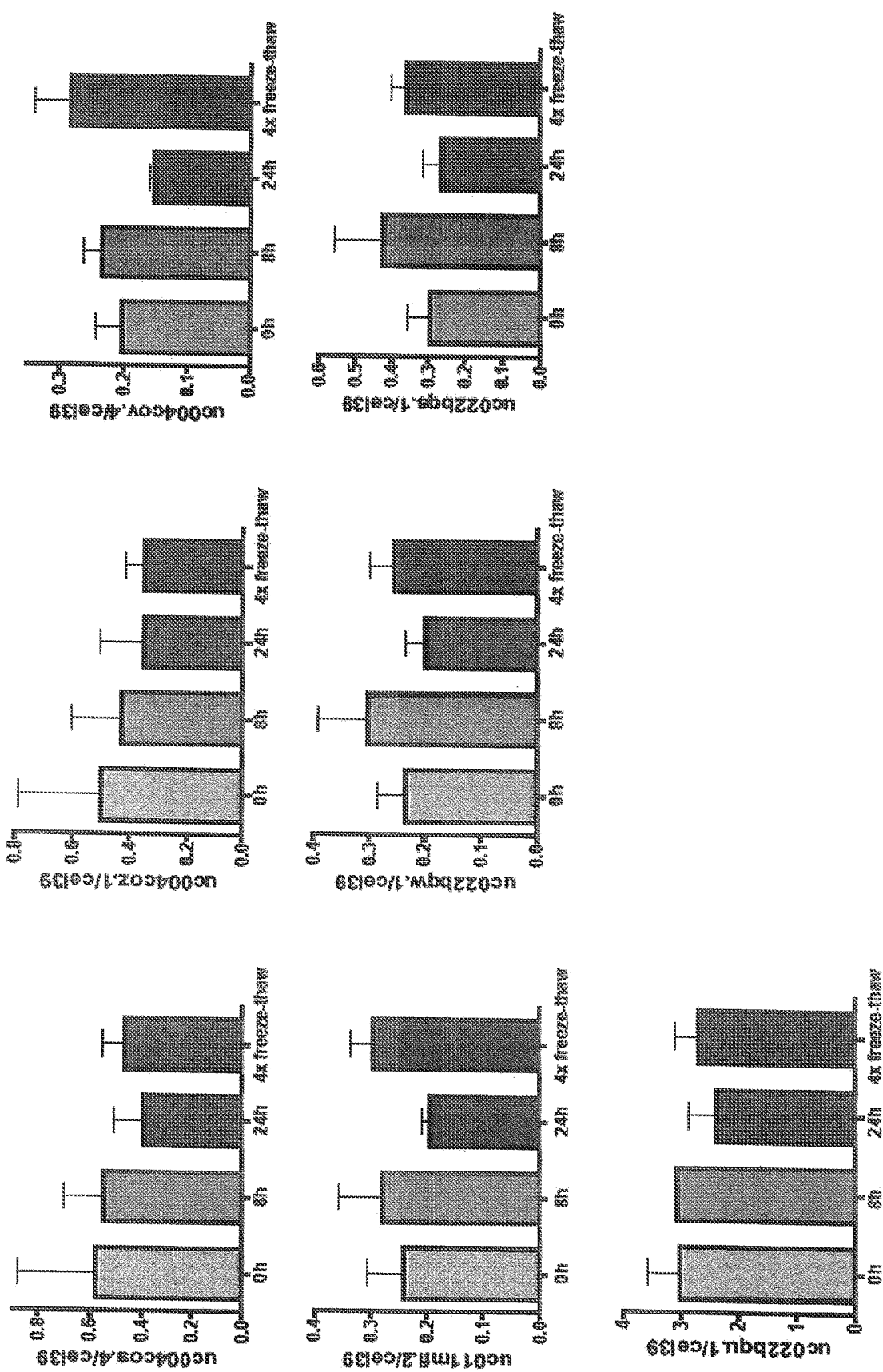

FIG. 7: Detection of seven different lncRNAs in plasma of three healthy controls. RNA was isolated from fresh plasma (0h) as well as from plasma kept on room temperature for up to 24 h and from plasma subjected to 4 freeze/thaw cycles.

The examples illustrate the invention.

EXAMPLE 1—METHODS

Heart Failure Patient Populations

The strategy of lncRNA screening and validation is depicted in FIG. 1. A potential association between detectable lncRNAs in EDTA-plasma and presence of future LV-remodeling post MI was analyzed in the REVE-2 cohort. This prospective multicentre study was designed to analyze the association between circulating biomarkers and LV-remodeling (Fertin M et al., Usefulness of serial assessment of B-type natriuretic peptide, troponin I, and C-reactive protein to predict left ventricular remodeling after acute myocardial infarction (from the REVE-2 study). *Am J Cardiol.* 2010; 106: 1410-1416). 246 patients with a first anterior wall Q-wave MI have been enrolled from February 2006 to September 2008. Inclusion criteria were hospitalization within 24 hours after symptom onset and at least three akinetic LV segments in the infarct zone at the pre-discharge echocardiography. Exclusion criteria were inadequate echographic image quality, life-limiting noncardiac disease, significant valvular disease, or prior Q-wave MI. The protocol required serial echographic studies at hospital discharge (day three to day seven) and three, and 12 months after MI to assess presence of LV-remodeling, which was defined as a >20% change in LV end-diastolic volume (LVEDV) between baseline and one year. Serial blood samples were taken at discharge (day three to day seven) and one, three, and 12 months after MI. The Institutional Ethics Committee (Centre Hospitalier Universitaire de Lille) approved the study; written informed consent was obtained from all patients. For patient characteristics see Table 1.

The association between the selected lncRNAs and HF characteristics and prognosis was then analyzed in two additional patient populations; these patients were selected from a consecutive series of patients with systolic HF (LV ejection fraction (LVEF) ≤45%) addressed to the Cardiology Department at Lille University. Patients who were ambulatory and clinically stable for at least two months underwent blood sampling for the study of prognostic biomarkers. The Institutional Ethics Committee (Centre Hospitalier Universitaire de Lille) approved the study; written informed consent was obtained from all patients. The design of this study has been previously published in detail (de Groote P et al., B-type natriuretic peptide and peak exercise oxygen consumption provide independent information for risk stratification in patients with stable congestive heart failure. *J Am Coll Cardiol.* 2004; 43: 1584-1589; and de Groote P et al., Right ventricular systolic function for risk stratification in patients with stable left ventricular systolic dysfunction: comparison of radionuclide angiography to echoDoppler parameters. *Eur Heart J.* 2012; 33: 2672-2679). It was first analyzed lncRNAs levels in 344 consecutive patients included from January 2006 to May 2010 (referred to as the HF cohort study). A follow-up was performed after three years to assess clinical outcome. For patient characteristics see Table 2. The prognostic value of the lncRNA was further assessed in an independent population of 198 patients included between November 1998 and December 2005 who underwent a prognostic evaluation including a clinical evaluation, echocardiography, cardiopulmonary exercise tests, and BNP measurement. (referred to as the HF case/control study). 99 patients were selected who died from cardiovascular death within three years after prognostic evaluation (cases); these 99 patients were matched (for age, sex, and HF etiology) with 99 HF patients who were alive after three years (controls). For patient characteristics see Table 3.

RNA Isolation from Plasma

For each patient, plasma was collected and processed as described earlier (Bauters C et al., Circulating miR-133a and miR-423-5p fail as biomarkers for left ventricular remodeling after myocardial infarction. *Int J Cardiol.* 2013; 3:168: 1837-40). Thus, RNA was isolated from 1526 samples (246 from the REVE 2 study collected over four different time points, 344 from the systolic HF cohort and 198 from the systolic HF case/control study) using the miRNeasy 96 Kit (Qiagen, #217061). As an internal spike-in control, *Caenorhabditis elegans* cel-miR-39 was added during the isolation process. Quality and integrity of the isolated RNA was verified by NanoDrop (Thermo scientific) and Bioanalyzer (Agilent). OD260/280 ratio ranged between 1.68 to 1.8 and RIN numbers ranged between 7.1 to 7.8.

Microarray Analysis of LncRNAs

For the initial lncRNA screening, plasma RNA was isolated from 15 male patients from the REVE2 cohort showing significant LV-remodeling 12 months after myocardial infarction and 15 male patients with no LV-remodeling (as defined earlier). Six RNA samples were obtained from the 30 patients by pooling RNA from five patients within one group as 'one sample'. Thus, three pooled RNA samples from 15 patients with LV-remodeling and three from patients without LV-remodeling were generated. These pools were subjected to microarray-based global transcriptome analysis. RNA was first pre-amplified and then subjected to microarrays (Arraystar Human LncRNA array; version 2.0), which allow simultaneous detection of 33,045 lncRNAs. To define a potential good biomarker candidate lncRNA, the following strategy was chosen: First all lncRNA transcripts that were included in the microarrays were sorted according to their average signal intensity. The signal intensity for each lncRNA transcript ranged between five (lowest value) to 17 (highest value). Only 1.3 to 4.3% of all lncRNA transcripts that are expressed from all somatic and sex chromosomes showed a signal intensity of >9 in plasma (Table 5). LncRNA detection was next validated by real time PCR. For this purpose, the isolated RNA was reverse transcribed with random primers (lncRNAs). Specific lncRNAs were amplified using primers listed in Table 6 and corresponding to SEQ ID NOs 9 to 22. *C. elegans*-miR-39 was amplified using a TaqMan assay as a normalization control.

LncRNA Stability Testings

Stable detection of seven different lncRNAs in plasma of three healthy controls was tested. This included testing lncRNA detection in plasma directly after blood withdrawal and keeping plasma at room temperature for 4 h, 8 h and 24 h. In addition the influence of four repetitive freeze/thaw cycles on lncRNA expression was tested. Overall, in all samples all seven investigated lncRNAs could be stably detected with no effects of keeping at room temperature or repetitive freeze/thaw cycles (FIG. 7).

Statistical Analysis

Statistical analyses were performed using R Statistical Package version 3.0. Results are presented as the mean±SD or number (percentages) of patients. In all statistical analyses, lncRNAs levels were log-transformed by taking the base two logarithm to account for the skewness of their distributions. Continuous variables were compared using unpaired Student's t-test. Discrete variables were compared using $X^2$ analysis. A p value <0.05 was considered statistically significant. Multivariate logistic regression was used to calculate odds ratios (OR) and corresponding 95% confidence intervals. OR were reported for a standard deviation increase. The associations of the baseline levels of the 7 candidate lncRNAs with LV-remodeling in the REVE-2 study were assessed using a logistic regression adjusted for age, sex, and LVEDV at baseline. In both HF populations, cardiovascular death was defined as deaths from cardiovascular causes, urgent transplantations (defined as United Network for Organ Sharing status one), or urgent left ventricular assist device implantation. The association of the selected lncRNA with the risk of cardiovascular death was assessed using a logistic regression adjusted for age, sex, ischemic etiology, and diabetes. In the case-control study, the independent prognostic value of the selected lncRNA was assessed by a logistic regression adjusted for age, sex, ischemic etiology, diabetes, NYHA class, LVEF, BNP, and peak exercise oxygen consumption (Peak VO$_2$). To illustrate the prognostic impact of the selected lncRNA in HF patients, its levels were categorized into quartiles.

EXAMPLE 2—CIRCULATING LNCRNAS FOR PREDICTING HEART CONDITIONS

Levels of Circulating LncRNAs are Altered During the Early Stage of Post-MI LV-Remodeling LncRNA arrays were performed from RNA derived from plasma of patients included in the LV-remodeling study (FIG. 1). The characteristics of the 246 patients included in this study are summarized in Table 1. One-year echocardiographic follow-up was completed for 226 (92%) patients. LV-remodeling, defined as a >20% change in LVEDV between baseline and 12 months, occurred in 87 (38.5%) patients. From this population, 15 male patients with high LV-remodeling (change in LVEDV=73±19%) and 15 male patients without LV-remodeling (change in LVEDV=−10±10%) with the same LVEDV baseline at discharge (high-remodelers: 49±11 ml/m$^2$ vs 49±12 ml/m$^2$ in non-remodelers) were selected. In an attempt to study alterations in circulating lncRNAs at early stage of post-MI LV-remodeling, microarrays were performed on RNA from plasma of these 30 patients at baseline.

Hierarchical clustering analysis clearly distinguished the two groups of patients based on a specific signature of detectable and significantly regulated circulating lncRNAs (FIG. 2A). A total of 768 lncRNA transcripts were specifically de-regulated (550 lncRNA transcripts up-regulated and 218 lncRNA transcripts down-regulated; each p<0.05) in patients that will develop LV-remodeling (FIG. 2B). Filteration all deregulated transcripts for high signal intensity (≥9) and at least 3-fold de-regulation yielded 15 lncRNA candidates, of which 7 could be consistently amplified in all individual samples that were used for microarrays. When the abundance of all detectable lncRNAs was correlated to their chromosomal origins, the highest percentage (77.78%) of high abundant lncRNAs (signal intensity >9) originated from the mitochondrial genome (chromosome M) (compared to 1.3 to 4.3% for somatic and sex-chromosomes). Thus, the majority of mitochondrial lncRNAs was abundantly present in plasma (Table 5). Interestingly, all seven lncRNAs that could be consistently amplified in all individual samples originate from the mitochondrial genome and all these lncRNAs were significantly down-regulated (p<0.05) in the initial microarray analysis. The expression level of these seven candidate lncRNAs was then assessed by independent real-time PCR in the entire study population of 246 patients at baseline. Levels of these seven lncRNAs were positively correlated with each other (Table 7). When validating in the total cohort, only lncRNAs uc004cos.4

(SEQ ID NO: 2 and uc022bqs.1 (SEQ ID NO:1 were significantly down-regulated and predicted future cardiac remodeling in patients (OR of 0.69 [0.49-0.94](P=0.022), and 0.62 [0.44-0.86](P=0.005), respectively; FIG. 3). Since these both lncRNAs levels were positively correlated (Table 7), uc022bqs.1 (which had the greatest association with LV-remodeling) was selected for further analyses. Because of its properties this lncRNA is referred as LIPCAR (SEQ ID NO: 1) in subsequent sections of the manuscript (Long Intergenic non-coding RNA Predicting CArdiac Remodeling).

LIPCAR Levels are Increased During Late Stages of Post-MI Remodeling

Next the level of LIPCAR was longitudinally studied in plasma samples obtained one, three and 12 months after MI in the patients of the REVE-2 cohort. In the overall study population, there was an increase in LIPCAR levels throughout the one year follow-up period. Importantly, as illustrated in FIG. 4, when assessed at one, three and 12 months, LIPCAR levels were significantly higher in patients developing LV-remodeling. Thus, in patients with LV-remodeling, circulating levels of LIPCAR are down-regulated at baseline, but significantly upregulated later on during the development of heart failure (HF).

LIPCAR Levels are Elevated in Chronic Heart Failure Patients

Since LIPCAR was upregulated in the late stages of patients developing LV-remodeling post-MI, it was hypothesized that its circulating levels could also be elevated in patients with chronic HF. This was tested in another independent cohort of 344 patients with systolic HF (see Table 2 for patient characteristics). These patients had similar age and sex characteristics compared to the patients of the LV-remodeling study; they also received angiotensin-converting enzyme inhibitors and beta-blockers in most cases. HF was of ischemic etiology in about half of the cases. These patients had more advanced disease than the patients of the LV-remodeling study as shown by their lower LV ejection fraction. As illustrated in FIG. 5, LIPCAR levels were even higher in chronic HF than in patients with ongoing LV-remodeling one year after MI; this was not only apparent for patients with ischemic HF but also for patients with non ischemic HF (both P<0.0001 vs patients with LV-remodeling one year after MI). It was next studied whether LIPCAR levels may be associated with the risk of future cardiovascular events in chronic HF patients. During a three-year clinical follow-up, 39 HF patients with LIPCAR measurements at inclusion died from cardiovascular causes, while 254 were still alive after three years. LIPCAR levels at inclusion were significantly associated with the risk of cardiovascular death (OR (adjusted for age, sex, ischemic etiology, and diabetes mellitus)=1.42 [1.02-2.01], P=0.04).

LIPCAR as a Prognostic Indicator for Chronic HF

Since the observation that elevated LIPCAR levels may be associated with future cardiovascular death was derived from a population with a limited number of events, the prognostic value of this potential biomarker in a third population of chronic systolic HF patients was further studied. As explained earlier, this was a case-control study in which cases died from cardiovascular death within three years after prognostic evaluation, while controls were still alive after three years. As shown in Table 3, cases had higher NYHA class and BNP levels, and lower Peak $VO_2$. As shown in FIG. 6, LIPCAR levels at the time of prognostic evaluation were higher in case patients than in control patients (P<0.0001). Compared with patients in the first quartile for LIPCAR levels, patients in the third and fourth quartiles had increased cardiovascular mortality (OR=6.58 [2.76-16.67], and 13.23 [5.19-36.8], respectively, both P<0.0001) (Table 4). In a model adjusting for age, sex, ischemic etiology, diabetes mellitus, NYHA class, LVEF, BNP, and Peak $VO_2$, the level of LIPCAR used as a continuous variable was an independent predictor of three-year cardiovascular mortality with an adjusted OR of 4.16 [2.67-6.90] (P<0.0001); similar results were obtained when LIPCAR levels were categorized into quartiles (third vs first quartile, OR=17.12 [5.19-66.61] (P<0.0001); fourth vs first quartile, OR=32.58 [9.62-131.00] (P<0.0001).

TABLE 1

Characteristics of the patients included in the LV-remodeling study (n = 246)

| | |
|---|---|
| Age (years ± SD) | 57 ± 14 |
| Women | 46 (19%) |
| Diabetes mellitus | 51 (21%) |
| First anterior myocardial infarction | 246 (100%) |
| Initial reperfusion therapy: | |
| Primary percutaneous coronary intervention | 128 (52%) |
| Thrombolysis alone | 28 (11%) |
| Thrombolysis and rescue percutaneous coronary intervention | 59 (24%) |
| No reperfusion | 31 (13%) |
| Peak creatine kinase (IU ± SD) | 3018 ± 2376 |
| HF (Killip class ≥2) during hospitalization | 79 (32%) |
| LVEF (% ± SD) | 49 ± 8 |
| Medications at discharge: | |
| Antiplatelet therapy | 246 (100%) |
| Beta-blockers | 238 (97%) |
| ACE inhibitors | 238 (97%) |
| Statins | 231 (94%) |
| One-year echocardiographic follow-up: | |
| Number of patients with follow-up | 226 (92%) |
| Change in LVEDV between baseline and 1 year (% ± SD) | 21 ± 27 |
| LV-remodeling [1] | 87 (38.5% [2]) |

LV indicates left ventricular; SD, standard deviation; IU, international units; EF, ejection fraction; ACE, angiotensin-converting enzyme; EDV, end-diastolic volume.
[1] defined as a >20% change in LVEDV between baseline and 12 months.
[2] out of the 226 patients with echocardiographic follow-up.

TABLE 2

Characteristics of the patients included in the systolic HF cohort study

| | Ischemic HF (n = 164) | Non ischemic HF (n = 180) |
|---|---|---|
| Age (yrs ± SD) | 56 ± 11 | 53 ± 11 |
| Women | 28 (17%) | 41 (23%) |
| Diabetes mellitus | 50 (30%) | 37 (21%) |
| NYHA class: | | |
| 1/2 | 136 (83%) | 153 (85%) |
| 3 | 28 (17%) | 27 (15%) |
| LVEF (% ± SD) | 33 ± 9 | 34 ± 10 |
| ACE inhibitors | 130 (79%) | 148 (82%) |
| Beta-blockers | 159 (97%) | 166 (92%) |
| Diuretics | 123 (75%) | 145 (81%) |

NYHA indicates New York Heart Association;
LVEF, left ventricular ejection fraction;
ACE, angiotensin-converting enzyme

TABLE 3

Characteristics of the patients included in the systolic HF case/control study

|  | No cardiovascular death (n = 99) | Cardiovascular death (n = 99) | P value |
|---|---|---|---|
| Age (yrs ± SD) | 59 ± 11 | 59 ± 11 | — |
| Women | 8 (8%) | 8 (8%) | — |
| HF etiology: | | | |
| Ischemic | 58 (59%) | 58 (59%) | — |
| Non ischemic | 41 (41%) | 41 (41%) | — |
| Diabetes mellitus | 33 (33%) | 34 (34%) | 0.901 |
| NYHA class: | | | |
| 1 or 2 | 81 (82%) | 63 (64%) | 0.004 |
| 3 | 18 (18%) | 36 (36%) | 0.004 |
| LVEF (% ± SD) | 29 ± 9 | 28 ± 10 | 0.490 |
| Peak VO$_2$ (ml/min/kg ± SD) | 17.2 ± 4.9 | 13.5 ± 3.7 | <0.0001 |
| BNP | | | |
| Low | 40 (42%) | 17 (18%) | |
| Intermediate | 33 (34%) | 42 (45%) | 0.002 |
| High | 23 (24%) | 35 (37%) | |
| ACE inhibitors | 92 (93%) | 92 (93%) | 1 |
| Beta-blockers | 94 (95%) | 90 (91%) | 0.407 |
| Diuretics | 77 (78%) | 87 (88%) | 0.06 |

NYHA indicates New York Heart Association; LVEF, left ventricular ejection fraction; peak VO2, peak exercise oxygen consumption; BNP, B-type natriuretic peptide; ACE, angiotensin-converting enzyme.
The levels of BNP were categorized as low (deciles 1, 2, and 3), intermediate (deciles 4, 5, 6, and 7), and high (deciles 8, 9, and 10)

TABLE 4

Association of LIPCAR levels with cardiovascular mortality in the systolic HF case/control study (n = 198 patients)

|  | Odds Ratio | 95% CI | P value |
|---|---|---|---|
| LIPCAR (log2), per 1 SD | 3.18 | 2.24-4.67 | <0.0001 |
| LIPCAR (quartiles of arbitrary units) | | | |
| 0-0.102 | — | — | — |
| 0.102-0.18 | 1.24 | 0.5-3.11 | 0.6 |
| 0.18-2.56 | 6.58 | 2.76-16.67 | <0.0001 |
| 2.56-89.5 | 13.23 | 5.19-36.8 | <0.0001 |

Adjusted on age, gender, HF etiology, and diabetes mellitus;
CI indicates confidence interval

TABLE 5

LncRNAs detected with average signal intensity ≥9 in all 6 microarrays.

| Chr. no | Total LncRNA represented | LncRNAs with signal intensity ≥9 | % |
|---|---|---|---|
| 1 | 2139 | 37 | 1.73 |
| 2 | 1553 | 36 | 2.32 |
| 3 | 1077 | 23 | 2.14 |
| 4 | 779 | 16 | 2.05 |
| 5 | 1074 | 35 | 3.26 |
| 6 | 984 | 16 | 1.63 |
| 7 | 1049 | 33 | 3.15 |
| 8 | 870 | 19 | 2.18 |
| 9 | 765 | 21 | 2.75 |
| 10 | 980 | 15 | 1.53 |
| 11 | 1414 | 28 | 1.98 |
| 12 | 1105 | 26 | 2.35 |
| 13 | 470 | 14 | 2.98 |
| 14 | 686 | 17 | 2.48 |
| 15 | 972 | 26 | 2.67 |
| 16 | 1028 | 25 | 2.43 |
| 17 | 1263 | 35 | 2.77 |
| 18 | 353 | 7 | 1.98 |
| 19 | 469 | 6 | 1.28 |
| 20 | 660 | 9 | 1.36 |
| 21 | 299 | 13 | 4.35 |
| 22 | 546 | 14 | 2.56 |
| m | 9 | 7 | 77.78 |
| x | 451 | 12 | 2.66 |
| y | 294 | 2 | 0.68 | m = mitochondrial genome;
x/y = sex chromosomes

TABLE 6

Oligonucleotide sequences used for lncRNA detection

| lncRNA description | SEQ ID lncRNA | Oligonucleotide Sequence Forward primer | SEQ ID Forward primer | Oligonucleotide Sequence Reverse primer | SEQ ID Reverse primer |
|---|---|---|---|---|---|
| uc022bqs.1 | SEQ ID NO. 1 | TAAAGGATGCGTAGGGATGG | SEQ ID NO. 19 | TTCATGATCACGCCCTCATA | SEQ ID NO. 20 |
| uc004coz.1 | SEQ ID NO. 6 | CAAATCCCTTCTCGTCCCCA | SEQ ID NO. 11 | TACCCCCAAGTGTTATGGGC | SEQ ID NO. 12 |
| uc004cov.4 | SEQ ID NO. 4 | TTCCCCAACCTTTTCCTCCG | SEQ ID NO. 13 | TGGATAAGTGGCGTTGGCTT | SEQ ID NO. 14 |
| uc011mfi.2 | SEQ ID NO. 7 | ACCGGGGGTATACTACGGTC | SEQ ID NO. 15 | GCTCTAGAGGGGTAGAGGG | SEQ ID NO. 16 |
| uc022bqw.1 | SEQ ID NO. 5 | TATCCGCCATCCCATACATT | SEQ ID NO. 17 | GGTGATTCCTAGGGGGTTGT | SEQ ID NO. 18 |
| uc004cos.4 | SEQ ID NO. 2 | ATGCCAACCTCCTACTCCT | SEQ ID NO. 9 | TAGATGTGGCGGGTTTTAGG | SEQ ID NO. 10 |
| uc022bqu.1 | SEQ ID NO. 8 | GCGGCTTCGACCCTATATCC | SEQ ID NO. 21 | AGGGCTCATGGTAGGGGTAA | SEQ ID NO. 22 |

TABLE 7

Correlation coefficients for seven lncRNAs

|  | uc004cos.4 | uc004coz.1 | uc004cov.4 | uc011mfi.2 | uc022bqw.1 | uc022bqs.1 |
|---|---|---|---|---|---|---|
| uc004coz.1 | 0.88 | | | | | |
| uc004cov.4 | 0.64 | 0.83 | | | | |
| uc011mfi.2 | 0.61 | 0.77 | 0.84 | | | |
| uc022bqw.1 | 0.55 | 0.55 | 0.38 | 0.63 | | |

TABLE 7-continued

Correlation coefficients for seven lncRNAs

| | uc004cos.4 | uc004coz.1 | uc004cov.4 | uc011mfi.2 | uc022bqw.1 | uc022bqs.1 |
|---|---|---|---|---|---|---|
| uc022bqs.1 | 0.62 | 0.58 | 0.38 | 0.60 | 0.96 | |
| uc022bqu.1 | 0.60 | 0.78 | 0.92 | 0.88 | 0.56 | 0.52 |

The invention claimed is:

1. A method for predicting mortality of a test patient with chronic heart failure, comprising:
   (a) detecting the expression level of long non-coding RNA (lncRNA) of SEQ ID NO 1 in a blood sample obtained from said test patient with chronic heart failure,
   (b) comparing said expression level of the lncRNA with the expression level of this lncRNA in a blood sample obtained from a control patient with chronic heart failure,
      wherein the control patient was alive at least three years after diagnosis of the chronic heart failure, and a greater than 2-fold overexpression of the lncRNA in the test patient's blood sample as compared to the control patient's blood sample is indicative of an enhanced likelihood for future cardiovascular death of the test patient; and/or
   (b') comparing said expression level of the lncRNA with the expression level of this lncRNA in a blood sample obtained from a control patient with chronic heart failure,
      wherein the control patient died from a cardiovascular event within about three years after diagnosis of chronic heart failure, and a greater than 2-fold under expression of lncRNA in the test patient's blood sample as compared to the control patient's blood sample is indicative of an enhanced likelihood for the long term survival of the test patient,
   wherein both the test patient and the control patient are human, and
   wherein detecting the expression level of the lncRNA comprises
      quantitative PCR using at least one primer selected from the group consisting of SEQ ID NOs 19 and 20, or
      a template/RNA amplification method using at least one primer selected from the group consisting of SEQ ID NOs 19 and 20 followed by determining the expression level of the lncRNA using a fluorescence- or luminescence-based quantification method.

2. The method of claim 1, wherein the chronic heart failure is systolic heart failure.

3. A method for predicting cardiac remodeling after myocardial infarction in a test patient, comprising:
   (a) detecting the expression level of lncRNA of SEQ ID NO 1 in a blood sample obtained from said test patient after myocardial infarction, and
   (b) comparing said expression level of the lncRNA with the expression level of this lncRNA in a blood sample obtained from a control patient after myocardial infarction, wherein the control patient did not show cardiac remodeling after myocardial infarction, wherein
      (i) the blood samples have been obtained from said test patient and from said control patient within a time frame of about two weeks after myocardial infarction, and a greater than 2-fold under expression of the lncRNA in the test patient's blood sample as compared to the control patient's blood sample is indicative for future cardiac remodeling in the test patient, and/or
      (ii) the blood samples have been obtained from said test patient and from said control patient more than about two weeks after myocardial infarction, and a greater than 2-fold overexpression of the lncRNA in the test patient's blood sample as compared to the control patient's blood sample is indicative for future cardiac remodeling in the test patient,
   wherein both the test patient and the control patient are human, and
   wherein detecting the expression level of the lncRNA comprises
      quantitative PCR using at least one primer selected from the group consisting of SEQ ID NOs 19 and 20, or
      a template/RNA amplification method using at least one primer selected from the group consisting of SEQ ID NOs 19 and 20 followed by determining the expression level of the lncRNA using a fluorescence- or luminescence-based quantification method.

4. The method of claim 3, wherein cardiac remodeling comprises or is left ventricular remodeling.

5. The method of claim 3, wherein the time frame of about two weeks is a time frame of about 10 days.

6. The method of claim 3, wherein the more than about two weeks are more than about three weeks.

7. The method of claim 1, wherein the blood samples are plasma or serum samples.

8. The method of claim 1, wherein the method comprises, prior to detecting the expression level of the long non-coding RNA, a pre-amplification step of the RNA within the test patient's blood sample and/or the control patient's blood sample.

9. The method of claim 5, wherein the time frame of about two weeks is a time frame of about 7 days.

10. The method of claim 6, wherein the more than about two weeks are more than about four weeks.

11. The method of claim 1, wherein the quantitative PCR is quantitative real time PCR.

12. The method of claim 1, wherein detecting the expression level of the lncRNA comprises
   quantitative PCR using the primer sequences of SEQ ID NOs 19 and 20, or
   a template/RNA amplification method using the primer sequences of SEQ ID NOs 19 and 20 followed by determining the expression level of the lncRNA using a fluorescence- or luminescence-based quantification method.

13. The method of claim 3, wherein detecting the expression level of the lncRNA comprises
   quantitative PCR using the primer sequences of SEQ ID NOs 19 and 20, or
   a template RNA amplification method using the primer sequences of SEQ ID NOs 19 and 20 followed by determining the expression level of the lncRNA using a fluorescence- or luminescence-based quantification method.

* * * * *

SEQUENCE LISTING

```
<160> NUMBER OF SEQ ID NOS: 22

<210> SEQ ID NO 1
<211> LENGTH: 781
<212> TYPE: DNA
<213> ORGANISM: Homo sapiens
<220> FEATURE:
<221> NAME/KEY: source
<222> LOCATION: 1..781
<223> OTHER INFORMATION: UC022BQS.1

<400> SEQUENCE: 1
aggcccattt gagtattttg ttttcaatta gggagatagt tggtattagg attaggattg     60
ttgtgaagta tagtacggat gctacttgtc caatgatggt aaaagggtag cttactggtt    120
gtcctccgat tcaggttaga atgaggaggt ctgcggctag gagtcaataa agtgattggc    180
ttagtgggcg aaatattatg ctttgttgtt tggatatatg gaggatgggg attattgcta    240
ggatgaggat ggatagtaat agggcaagga cgcctcctag tttgttaggg acggatcgga    300
gaattgtgta ggcgaatagg aaatatcatt cgggcttgat gtggggaggg gtgtttaagg    360
ggttggctag ggtataattg tctgggtcgc ctggttctag gaataatggg ggaagtatgt    420
aggagttgaa gattagtccg ccgtagtcgg tgtactcgta ggttcagtac cattggtggc    480
caattgattt gatggtaagg gagggatcgt tgacctcgtc tgttatgtaa aggatgcgta    540
gggatgggag ggcgatgagg actaggatga tggcgggcag gatagttcag acggtttcta    600
tttcctgagc gtctgagatg ttagtattag ttagttttgt tgtgagtgtt aggaaaaggg    660
catacaggac taggaagcag ataaggaaaa tgattatgag ggcgtgatca tgaaaggtga    720
taagctcttc tatgataggg gaagtagcgt cttgtagacc tacttgcgct gcatgtgcca    780
t                                                                    781

<210> SEQ ID NO 2
<211> LENGTH: 2509
<212> TYPE: DNA
<213> ORGANISM: Homo sapiens
<220> FEATURE:
<221> NAME/KEY: source
<222> LOCATION: 1..2509
<223> OTHER INFORMATION: UC004COS.4

<400> SEQUENCE: 2
gaaattgaaa cctggcgcaa tagatatagt accgcaaggg aaagatgaaa aattataacc     60
aagcataata tagcaaggac taaccccctat accttctgca taatgaatta actagaaata   120
actttgcaag gagagccaaa gctaagaccc ccgaaaccag acgagctacc taagaacagc    180
taaaagagca caccgtctca tgtagcaaaa tagtgggaag attttataggt agaggcgaca   240 aacctaccga gcctggtgat agctggttgt ccaagataga atcttagttc aactttaaat    300
ttgcccacag aaccctctaa atcccccttgt aaatttaact gttagtccaa agaggaacag    360
ctctttggac actaggaaaa aaccttgtag agagagtaaa aaatttaaca cccatagtag    420
```

```
gcctaaaagc agccaccaat taagaaagcg ttcaagctca acacccacta cctaaaaaat    480
cccaaacata taactgaact cctcacaccc aattggacca atctatcacc ctatagaaga    540
actaatgtta gtataagtaa catgaaaaca ttctcctccg cataagcctg cgtcagatca    600
aaacactgaa ctgacaatta acagcccaat atctacaatc aaccaacaag tcattattac    660
cctcactgtc aacccaacac aggcatgctc ataaggaaag gttaaaaaaa gtaaaggaa     720 ctcggcaaac cttaccccgc ctgtttacca aaaacatcac ctctagcatc accagtatta    780
gaggcaccgc ctgcccagtg acacatgttt aacggccgcg gtaccctaac cgtgcaaagg    840
tagcataatc acttgttcct taaataggga cctgtatgaa tggctccacg agggttcagc    900
tgtctcttac ttttaaccag tgaaattgac ctgcccgtga agaggcgggc atgacacagc    960
aagacgagaa gaccctatgg agctttaatt tattaatgca aacagtacct aacaaaccca   1020
caggtcctaa actaccaaac ctgcattaaa aatttcggtt ggggcgacct cggagcagaa   1080
cccaacctcc gagcagtaca tgctaagact tcaccagtca aagcgaacta ctatactcaa   1140
ttgatccaat aacttgacca acggaacaag ttaccctagg gataacagcg caatcctatt   1200
ctagagtcca tatcaacaat agggtttacg acctcgatgt tggatcagga catcccgatg   1260
gtgcagccgc tattaaaggt tcgtttgttc aacgattaaa gtcctacgtg atctgagttc   1320
agaccggagt aatccaggtc ggtttctatc tacttcaaat tcctccctgt acgaaaggac   1380
aagagaaata aggcctactt cacaaagcgc cttcccccgt aaatgatatc atctcaactt   1440
agtattatac ccacacccac ccaagaacag ggtttgttaa gatggcagag cccggtaatc   1500
gcataaaact taaaacttta cagtcagagg ttcaattcct cttcttaaca acatacccat   1560
ggccaacctc ctactcctca ttgtacccat tctaatcgca atggcattcc taatgcttac   1620
cgaacgaaaa attctaggct atatacaact acgcaaaggc cccaacgttg taggccccta   1680
cgggctacta caacccttcg ctgacgccat aaaactcttc accaaagagc cctaaaaacc   1740
cgccacatct accatcaccc tctacatcac cgccccgacc ttagctctca ccatcgctct   1800
tctactatga accccctcc ccataccaa cccctggtc aacctcaacc taggcctcct    1860
atttattcta gccacctcta gcctagccgt ttactcaatc ctctgatcag ggtgagcatc   1920
aaactcaaac tacgccctga tcggcgcact gcgagcagta gcccaaacaa tctcatatga   1980
agtcacccta gccatcattc tactatcaac attactaata gtggctcctt ttaacctctc   2040 caccttatc acaacacaag aacacctctg attactcctg ccatcatgac ccttggccat   2100
aatatgattt atctccacac tagcagagac caaccgaacc cccttcgacc ttgccgaagg   2160
ggagtccgaa ctagtctcag gcttcaacat cgaatacgcc gcaggcccct tcgccctatt   2220
cttcatagcc gaatacacaa acattattat aataaacacc ctcaccacta caatcttcct   2280
aggaacaaca tatgacgcac tctcccctga actctacaca acatattttg tcaccaagac   2340
cctacttcta acctccctgt tcttatgaat tcgaacagca taccccgat tccgctacga   2400 ccaactcata cacctcctat gaaaaaactt cctaccactc accctagcat tacttatatg   2460
atatgtctcc atacccatta caatctccag cattccccct caaacctaa               2509
```

<210> SEQ ID NO 3
<211> LENGTH: 1242
<212> TYPE: DNA
<213> ORGANISM: Homo sapiens
<220> FEATURE:
<221> NAME/KEY: source
<222> LOCATION: 1..1242

<223> OTHER INFORMATION: UC004COX.4

<400> SEQUENCE: 3

```
ctacactcca actcatgaga cccacaacaa atagcccttc taaacgctaa tccaagcctc      60
acccccactac taggcctcct cctagcagca gcaggcaaat cagcccaatt aggtctccac    120
ccctgactcc cctcagccat agaaggcccc accccagtct cagccctact ccactcaagc    180
actatagttg tagcaggaat cttcttactc atccgcttcc accccctagc agaaaatagc    240
ccactaatcc aaactctaac actatgctta ggcgctatca ccactctgtt cgcagcagtc    300
tgcgccctta cacaaaatga catcaaaaaa atcgtagcct tctccacttc aagtcaacta    360
ggactcataa tagttacaat cggcatcaac caaccacacc tagcattcct gcacatctgt    420
acccacgcct tcttcaaagc catactattt atgtgctccg ggtccatcat ccacaacctt    480
aacaatgaac aagatattcg aaaaatagga ggactactca aaaccatacc tctcacttca    540
acctccctca ccattggcag cctagcatta gcaggaatac ctttcctcac aggtttctac    600
tccaaagacc acatcatcga aaccgcaaac atatcataca caaacgcctg agccctatct    660
attactctca tcgctacctc cctgacaagc gcctatagca ctcgaataat tcttctcacc    720
ctaacaggtc aacctcgctt ccccacccttt actaacatta cgaaaataa ccccacccta    780
ctaaacccca ttaaacgcct ggcagccgga agcctattcg caggatttct cattactaac    840
aacatttccc ccgcatcccc cttccaaaca acaatccccc tctacctaaa actcacagcc    900
ctcgctgtca ctttcctagg acttctaaca gccctagacc tcaactacct aaccaacaaa    960
cttaaaataa aatcccccact atgcacattt tatttctcca acatactcgg attctaccct   1020
agcatcacac accgcacaat cccctatcta ggccttctta cgagccaaaa cctgccccta   1080
ctcctcctag acctaacctg actagaaaag ctattaccta aaacaatttc acagcaccaa   1140
atctccacct ccatcatcac ctcaacccaa aaaggcataa ttaaacttta cttcctctct   1200
ttcttcttcc cactcatcct aaccctactc ctaatcacat aa                       1242
```

<210> SEQ ID NO 4
<211> LENGTH: 1666
<212> TYPE: DNA
<213> ORGANISM: Homo sapiens
<220> FEATURE:
<221> NAME/KEY: source
<222> LOCATION: 1..1666
<223> OTHER INFORMATION: UC004COV.4

<400> SEQUENCE: 4

```
gcccctcatt tacataaata ttatactagc atttaccatc tcacttctag gaatactagt      60
atatcgctca cacctcatat cctccctact atgcctagaa ggaataatac tatcgctgtt    120
cattatagct actctcataa ccctcaacac ccactccctc ttagccaata ttgtgcctat    180
tgccatacta gtctttgccg cctgcgaagc agcggtgggc ctagccctac tagtctcaat    240
ctccaacaca tatggcctag actacgtaca taacctaaac ctactccaat gctaaaacta    300
atcgtcccaa caattatatt actaccactg acatgacttt ccaaaaagca cataatttga    360
atcaacacaa ccacccacag cctaattatt agcatcatcc cctactatt ttttaaccaa    420
atcaacaaca acctatttag ctgttcccca acctttcct ccgaccccct aacaaccccc    480
ctcctaatac taactacctg actcctaccc ctcacaatca tggcaagcca acgccactta    540
tccagcgaac cactatcacg aaaaaaactc tacctctcta tactaatctc ctacaaatc    600
tccttaatta taacattcac agccacagaa ctaatcatat tttatatctt cttcgaaacc    660
```

```
acacttatcc ccaccttggc tatcatcacc cgatgaggca accagccaga acgcctgaac      720
gcaggcacat acttcctatt ctacacccta gtaggctccc ttcccctact catcgcacta      780
atttacactc acaacaccct aggctcacta acattctac tactcactct cactgcccaa      840
gaactatcaa actcctgagc caacaactta atatgactag cttacacaat gcttttata      900 gtaaagatac ctctttacgg actccactta tgactcccta agcccatgt cgaagccccc      960 atcgctgggt caatagtact tgccgcagta ctcttaaaac taggcggcta tggtataata     1020
cgcctcacac tcattctcaa ccccctgaca aaacacatag cctacccctt ccttgtacta     1080
tccctatgag gcataattat aacaagctcc atctgcctac gacaaacaga cctaaaatcg     1140
ctcattgcat actcttcaat cagccacata gccctcgtag taacagccat tctcatccaa     1200
accccctgaa gcttcaccgg cgcagtcatt ctcataatcg cccacggact cacatcctca     1260
ttactattct gcctagcaaa ctcaaactac gaacgcactc acagtcgcat cataatcctc     1320
tctcaaggac ttcaaactct actcccacta atagcttttt gatgacttct agcaagcctc     1380
gctaacctcg ccttaccccc cactattaac ctactgggag aactctctgt gctagtaacc     1440
acgttctcct gatcaaatat cactctccta cttacaggac tcaacatact agtcacagcc     1500
ctatactccc tctacatatt taccacaaca caatgggct cactcaccca ccacattaac     1560
aacataaaac cctcattcac acgagaaaac accctcatgt tcatacacct atcccccatt     1620
ctcctcctat ccctcaaccc cgacatcatt accgggtttt cctctt                    1666
```

<210> SEQ ID NO 5
<211> LENGTH: 1032
<212> TYPE: DNA
<213> ORGANISM: Homo sapiens
<220> FEATURE:
<221> NAME/KEY: source
<222> LOCATION: 1..1032
<223> OTHER INFORMATION: UC022BQW.1

<400> SEQUENCE: 5

```
ttggcgcctg cctgatcctc caaatcacca caggactatt cctagccata cactactcac       60
cagacgcctc aaccgccttt tcatcaatcg cccacatcac tcgagacgta aattatggct      120
gaatcatccg ctaccttcac gccaatggcg cctcaatatt ctttatctgc ctcttcctac      180
acatcgggcg aggcctatat tacgatcat ttctctactc agaaacctga acatcggca       240 ttatcctcct gcttgcaact atagcaacag ccttcatagg ctatgtcctc ccgtgaggcc      300
aaatatcatt ctgaggggcc acagtaatta caaacttact atccgccatc ccatacattg      360
ggacagacct agttcaatga atctgaggag gctactcagt agacagtccc accctcacac      420
gattctttac ctttcacttc atcttacccct tcattattgc agcccagca gcactccacc       480 tcctattctt gcacgaaacg ggatcaaaca accccctagg aatcacctcc cattccgata      540
aaatcacctt ccaccttac tacacaatca agacgccct cggcttactt ctcttccttc       600
tctccttaat gacattaaca ctattctcac cagacctcct aggcgaccca gacaattata      660
ccctagccaa ccccttaaac accccctccc catcaagcc cgaatgatat ttcctattcg      720
cctacacaat tctccgatcc gtccctaaca aactaggagg cgtccttgcc ctattactat      780
ccatcctcat cctagcaata atccccatcc tccatatatc caaacaacaa agcataatat      840
ttcgcccact aagccaatca ctttattgac tcctagccgc agacctcctc attctaacct      900
gaatcggagg acaaccagta agctaccctt ttaccatcat tggacaagta gcatccgtac      960
```

| | |
|---|---:|
| tatacttcac aacaatccta atcctaatac caactatctc cctaattgaa aacaaaatac | 1020 |
| tcaaatgggc ct | 1032 |

<210> SEQ ID NO 6
<211> LENGTH: 573
<212> TYPE: DNA
<213> ORGANISM: Homo sapiens
<220> FEATURE:
<221> NAME/KEY: source
<222> LOCATION: 1..573
<223> OTHER INFORMATION: UC004COZ.1

<400> SEQUENCE: 6

| | |
|---|---:|
| aagattctaa tttaaactat tctctgttct ttcatgggga agcagatttg ggtaccaccc | 60 |
| aagtattgac tcacccatca acaaccgcta tgtatttcgt acattactgc cagccaccat | 120 |
| gaatattgta cggtaccata atacttgac cacctgtagt acataaaaac ccaacccaca | 180 |
| tcaaaccccc ccccccatg cttacaagca agtacagcaa tcaaccttca actatcacac | 240 |
| atcaactgca actccaaagc caccctcac ccactaggat accaacaaac ctacccaccc | 300 |
| ttaacagtac atagtacata aagtcattta ccgtacatag cacattacag tcaaatccct | 360 |
| tctcgtcccc atggatgacc cccctcagat aggggtccct tgaccaccat cctccgtgaa | 420 |
| atcaatatcc cgcacaagag tgctactctc ctcgctccgg gcccataaca cttgggggta | 480 |
| gctaaagtga actgtatccg acatctggtt cctacttcag ggccataaag cctaaatagc | 540 |
| ccacacgttc cccttaaata agacatcacg atg | 573 |

<210> SEQ ID NO 7
<211> LENGTH: 1622
<212> TYPE: DNA
<213> ORGANISM: Homo sapiens
<220> FEATURE:
<221> NAME/KEY: source
<222> LOCATION: 1..1622
<223> OTHER INFORMATION: UC011MFI.2

<400> SEQUENCE: 7

| | |
|---|---:|
| atggcacatg cagcgcaagt aggtctacaa gacgctactt cccctatcat agaagagctt | 60 |
| atcacctttc atgatcacgc cctcataatc attttcctta tctgcttcct agtcctgtat | 120 |
| gccctttttcc taaacactcac aacaaaacta actaatacta acatctcaga cgctcaggaa | 180 |
| atagaaaccg tctgaactat cctgcccgcc atcatcctag tcctcatcgc cctcccatcc | 240 |
| ctacgcatcc tttacataac agacgaggtc aacgatccct cccttaccat caaatcaatt | 300 |
| ggccaccaat ggtactgaac ctacgagtac accgactacg gcggactaat cttcaactcc | 360 |
| tacatacttc ccccattatt cctagaacca ggcgacctgc gactccttga cgttgacaat | 420 |
| cgagtagtac tcccgattga agcccccatt cgtataataa ttacatcaca agacgtcttg | 480 |
| cactcatgag ctgtccccac attaggctta aaaacagatg caattcccgg acgtctaaac | 540 |
| caaaccactt tcaccgctac acgaccgggg gtatactacg gtcaatgctc tgaaatctgt | 600 |
| ggagcaaacc acagtttcat gcccatcgtc ctagaattaa ttccccctaaa aatctttgaa | 660 |
| atagggcccg tatttaccct atagcacccc ctctacccc tctagagccc actgtaaagc | 720 |
| taacttagca ttaaccttt aagttaaaga ttaagagaac caacacctct ttacagtgaa | 780 |
| atgccccaac taaatactac cgtatggccc accataatta ccccatact ccttacacta | 840 |
| ttcctcatca cccaactaaa aatattaaac acaaactacc acctacctcc ctcaccaaag | 900 |
| cccataaaaa taaaaaatta taacaaaccc tgagaaccaa aatgaacgaa atctgttcg | 960 |

```
cttcattcat tgcccccaca atcctaggcc tacccgccgc agtactgatc attctatttc    1020
cccctctatt gatccccacc tccaaatatc tcatcaacaa ccgactaatc accacccaac    1080
aatgactaat caaactaacc tcaaaacaaa tgatagccat acacaacact aaaggacgaa    1140
cctgatctct tatactagta tccttaatca tttttattgc cacaactaac ctcctcggac    1200
tcctgcctca ctcatttaca ccaaccaccc aactatctat aaacctagcc atggccatcc    1260
ccttatgagc gggcgcagtg attataggct ttcgctctaa gattaaaaat gccctagccc    1320
acttcttacc acaaggcaca cctacacccc ttatccccat actagttatt atcgaaacca    1380
tcagcctact cattcaacca atagccctgg ccgtacgcct aaccgctaac attactgcag    1440
gccacctact catgcaccta attggaagcg ccaccctagc aatatcaacc attaaccttc    1500
cctctacact tatcatcttc acaattctaa ttctactgac tatcctagaa atcgctgtcg    1560
ccttaatcca agcctacgtt ttcacacttc tagtaagcct ctacctgcac gacaacacat    1620
aa                                                                  1622

<210> SEQ ID NO 8
<211> LENGTH: 346
<212> TYPE: DNA
<213> ORGANISM: Homo sapiens
<220> FEATURE:
<221> NAME/KEY: source
<222> LOCATION: 1..346
<223> OTHER INFORMATION: UC022BQU.1

<400> SEQUENCE: 8
ataaacttcg ccttaatttt aataatcaac accctcctag ccttactact aataattatt     60
acattttgac taccacaact caacggctac atagaaaaat ccacccctta cgagtgcggc    120
ttcgacccta tatccccgc ccgcgtccct ttctccataa aattcttctt agtagctatt    180
accttcttat tatttgatct agaaattgcc ctccttttac ccctaccatg agccctacaa    240
acaactaacc tgccactaat agttatgtca tccctcttat taatcatcat cctagcccta    300
agtctggcct atgagtgact acaaaaagga ttagactgaa ccgaat                   346

<210> SEQ ID NO 9
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc004cos.4 forward primer

<400> SEQUENCE: 9
atggccaacc tcctactcct                                                 20

<210> SEQ ID NO 10
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc004cos.4 reverse primer

<400> SEQUENCE: 10
tagatgtggc gggttttagg                                                 20

<210> SEQ ID NO 11
```

```
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc004coz.1 forward primer

<400> SEQUENCE: 11
caaatccctt ctcgtcccca                                              20

<210> SEQ ID NO 12
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc004coz.1 reverse primer

<400> SEQUENCE: 12
tacccccaag tgttatgggc                                              20

<210> SEQ ID NO 13
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc004cov.4 forward primer

<400> SEQUENCE: 13
ttccccaacc ttttcctccg                                              20

<210> SEQ ID NO 14
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc004cov.4 reverse primer

<400> SEQUENCE: 14
tggataagtg gcgttggctt                                              20

<210> SEQ ID NO 15
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc011mfi.2 forward primer

<400> SEQUENCE: 15
accgggggta tactacggtc                                              20

<210> SEQ ID NO 16
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc011mfi.2 reverse primer

<400> SEQUENCE: 16
```

```
gctctagagg gggtagaggg                                               20

<210> SEQ ID NO 17
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc022bqw.1 forward primer

<400> SEQUENCE: 17
tatccgccat cccatacatt                                               20

<210> SEQ ID NO 18
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc022bqw.1 reverse primer

<400> SEQUENCE: 18
ggtgattcct aggggttgt                                                20

<210> SEQ ID NO 19
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc022bqs.1 forward primer

<400> SEQUENCE: 19
taaaggatgc gtagggatgg                                               20

<210> SEQ ID NO 20
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc022bqs.1 reverse primer

<400> SEQUENCE: 20
ttcatgatca cgccctcata                                               20

<210> SEQ ID NO 21
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: uc022bqu.1 forward primer

<400> SEQUENCE: 21
gcggcttcga ccctatatcc                                               20

<210> SEQ ID NO 22
<211> LENGTH: 20
<212> TYPE: DNA
<213> ORGANISM: Artificial Sequence
<220> FEATURE:
```

```
<221> NAME/KEY: source
<222> LOCATION: 1..20
<223> OTHER INFORMATION: uc022bqu.1 reverse primer

<400> SEQUENCE: 22
agggctcatg gtaggggtaa                                              20
```